(12) United States Patent
Kim

(10) Patent No.: US 9,289,445 B2
(45) Date of Patent: Mar. 22, 2016

(54) COMPOSITIONS AND METHODS FOR TREATING OR PREVENTING A RETROVIRUS INFECTION

(75) Inventor: Baek Kim, Atlanta, GA (US)

(73) Assignee: University of Rochester, Rochester, NY (US)

( * ) Notice: Subject to any disclaimer, the term of this patent is extended or adjusted under 35 U.S.C. 154(b) by 63 days.

(21) Appl. No.: 13/980,836

(22) PCT Filed: Oct. 4, 2011

(86) PCT No.: PCT/US2011/054693
§ 371 (c)(1),
(2), (4) Date: Nov. 1, 2013

(87) PCT Pub. No.: WO2012/099630
PCT Pub. Date: Jul. 26, 2012

(65) Prior Publication Data
US 2014/0057864 A1    Feb. 27, 2014

Related U.S. Application Data

(60) Provisional application No. 61/434,690, filed on Jan. 20, 2011.

(51) Int. Cl.
| | |
|---|---|
| *A61K 31/7076* | (2006.01) |
| *A61K 45/06* | (2006.01) |
| *A61K 31/7072* | (2006.01) |
| *A61K 9/00* | (2006.01) |
| *A61F 6/04* | (2006.01) |
| *A61K 31/675* | (2006.01) |

(52) U.S. Cl.
CPC ............. *A61K 31/7076* (2013.01); *A61F 6/04* (2013.01); *A61K 9/0031* (2013.01); *A61K 9/0034* (2013.01); *A61K 31/675* (2013.01); *A61K 31/7072* (2013.01); *A61K 45/06* (2013.01)

(58) Field of Classification Search
USPC ...................................... 514/46, 51
See application file for complete search history.

(56) References Cited

U.S. PATENT DOCUMENTS

| 5,663,154 A | 9/1997 | Burns et al. |
| 6,914,052 B2 | 7/2005 | McLaughlin et al. |
| 2003/0119764 A1 | 6/2003 | Loeb et al. |

FOREIGN PATENT DOCUMENTS

EP    0043722 A1    1/1982

OTHER PUBLICATIONS

International Preliminary Report on Patentability, 2012.
Migliaccio, G. et al, Characterization of Resistance to Non-obligate Chain-terminating Ribonucleoside Analogs That Inhibit Hepatitis C Virus Replication in Vitro. The Journal of Biological Chemistry 2003, vol. 278, No. 49, pp. 49169-49170.
International Search Report of PCT/US2011/054693, 2012.

*Primary Examiner* — Kristin Vajda
(74) *Attorney, Agent, or Firm* — Riverside Law LLP

(57) ABSTRACT

The invention provides methods, compositions, and kits featuring a ribonucleoside chain terminator for use in preventing or inhibiting a retrovirus infection.

11 Claims, 19 Drawing Sheets

```
                          SEQUENCE LISTING

<160> NUMBER OF SEQ ID NOS: 8

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence: Synthetic
      6xHis tag

<400> SEQUENCE: 1

His His His His His His
1               5

<210> SEQ ID NO 2
<211> LENGTH: 20
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
tttttttttt tttttttttt                                                     20

<210> SEQ ID NO 3
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 3
cgcgccgaat tcccgct                                                        17

<210> SEQ ID NO 4
<211> LENGTH: 40
<212> TYPE: RNA
<213> ORGANISM: Artificial Sequence
<220> FEATURE:
<223> OTHER INFORMATION: Description of Artificial Sequence: Synthetic
      oligonucleotide

<400> SEQUENCE: 4
aagcuuggcu gcagaauauu gcuagcggga auucggcgcg                               40

<210> SEQ ID NO 5
<211> LENGTH: 23
```

```
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
cttataacga tcgcccttaa gcc                                              23

<210> SEQ ID NO 6
<211> LENGTH: 17
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
tcgcccttaa gccgcgc                                                     17

<210> SEQ ID NO 7
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 7
gaattcccgc tagcaatatt ct                                               22

<210> SEQ ID NO 8
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
tataacgatc gcccttaagc cg                                               22
```

COMPOSITIONS AND METHODS FOR TREATING OR PREVENTING A RETROVIRUS INFECTION

CROSS-REFERENCE TO RELATED APPLICATION

This application is the U.S. national stage application of PCT International Application No. PCT/US2011/054693, filed Oct. 4, 2011, which claims the benefit of U.S. Provisional Application No. 61/434,690, filed Jan. 20, 2011, the contents of which is are incorporated herein by reference in its entirety.

STATEMENT OF RIGHTS TO INVENTIONS MADE UNDER FEDERALLY SPONSORED RESEARCH

This work was supported by the following grants from the National Institutes of Health, Grant Nos: AI049781, 2P30-AI-050409, R01-AI-076535, 5R37-AI-041980, and 5R37-AI-025899. The Government has certain rights in this invention.

SEQUENCE LISTING

The instant application contains a Sequence Listing which has been submitted in ASCII format via EFS-Web and is hereby incorporated by reference in its entirety. Said ASCII copy, created on Sep. 24, 2013, is named 87869US(54739)_SL.txt and is 2,143 bytes in size.

BACKGROUND OF THE INVENTION

Lentiviruses such as human immunodeficiency virus are able to infect terminally differentiated/non-dividing cells, e.g., macrophages, as well as dividing activated CD4$^+$ T cells. Upon infection, viral genomic RNA is replicated into double stranded proviral DNA by a virally encoded DNA polymerase, reverse transcriptase (RT). Non-dividing cells harbor strikingly low cellular dNTP concentrations (20-40 nM) as compared to activated CD4$^+$ T cells (1-4 µM). Such limited cellular dNTP levels impose a kinetic stress on retroviral DNA synthesis catalyzed by viral RT in non-dividing cells.

Despite the replication barriers present in non-dividing cells, infection of non-dividing cells are a critical feature of retrovirus pathogenesis. For example, despite the strides that have been made in treating retrovirus infections, non-dividing cells remain a source of long-lived productive reservoirs of retrovirus infection in vivo. Accordingly, in order to improve current methods for preventing and treating retrovirus infection in non-dividing cells, there is a need to better understand how retroviruses are able to replicate in such a cellular environment. In particular, it is desirable to fully characterize the effects of the limited cellular dNTP levels in non-dividing cells on viral RT.

SUMMARY OF THE INVENTION

As described below, the present invention features methods, compositions, and kits for preventing, treating or otherwise inhibiting a retrovirus infection (e.g., HIV).

In one aspect, the invention provides methods for inhibiting retrovirus replication in a non-dividing viral host cell. In embodiments, the methods involve contacting a non-dividing cell having or at risk of developing a retroviral infection with a ribonucleoside chain terminator or an analog or derivative thereof. In embodiments, contacting the non-dividing cell with the ribonucleoside chain terminator results in inhibiting viral replication in the non-dividing cell.

In another aspect, the invention provides methods for inhibiting retrovirus replication in a macrophage. In embodiments, the methods involve contacting a macrophage having or at risk of developing a viral infection with a ribonucleoside chain terminator or an analog or derivative thereof. In embodiments, contacting the macrophage with the ribonucleoside chain terminator results in inhibiting viral replication in the macrophage.

In another aspect, the invention provides methods for inhibiting the establishment or persistence of a retrovirus reservoir in a non-dividing viral host cell. In embodiments, the methods involve contacting a non-dividing cell having or at risk of developing a viral infection with a ribonucleoside chain terminator or an analog or derivative thereof. In embodiments, contacting the non-dividing cell with the ribonucleoside chain terminator results in inhibiting the establishment or persistence of a retrovirus reservoir in the non-dividing cell.

In another aspect, the invention provides methods for inhibiting retrovirus replication in a non-dividing viral host cell. In embodiments, the methods involve contacting a non-dividing cell having or at risk of developing a retroviral infection with a ribonucleoside chain terminator or an analog or derivative thereof and at least one additional anti-retroviral agent. In embodiments, contacting the non-dividing cell with the ribonucleoside chain terminator and the anti-retroviral agent(s) results in inhibiting viral replication in the non-dividing cell.

In another aspect, the invention provides methods for inhibiting retrovirus replication in a subject. In embodiments, the methods involve administering to a subject having or at risk of developing a retroviral infection a ribonucleoside chain terminator or an analog or derivative thereof. In embodiments, administering the ribonucleoside chain terminator to the subject results in inhibiting viral replication in the subject.

In another aspect, the invention provides methods for inhibiting retrovirus replication in a subject. In embodiments, the methods involve administering to a subject having or at risk of developing a retroviral infection a ribonucleoside chain terminator or an analog or derivative thereof and at least one additional anti-retroviral agent. In embodiments, administering the ribonucleoside chain terminator and the anti-retroviral agent(s) to the subject results in inhibiting viral replication in the subject.

In another aspect, the invention provides methods for inhibiting retrovirus replication by using a topical formulation. In embodiments, the methods involve administering to a subject having or at risk of developing a retroviral infection a prophylactically effective amount of a topical formulation comprising a ribonucleoside chain terminator or an analog or derivative thereof. In further embodiments, the topical formulation contains at least one additional anti-retroviral agent. In embodiments, administering the topical formulation to the subject results in inhibiting viral replication in the subject.

In related embodiments, the topical formulation further comprises a pharmaceutically acceptable medium suitable for topical application. In related embodiments, the topical formulation is in the form of a spray, gel, cream, foam, lotion, ointment, salve, powder, or suppository. In related embodiments, the topical formulation is administered to the vagina, anus, or mouth of the subject. In related embodiments, the topical formulation is coated on a condom or is incorporated into a condom. In related embodiments, the topical formulation is provided in a separate container from the condom and is applied onto the condom prior to use.

In another aspect, the invention provides pharmaceutical compositions containing a ribonucleoside chain terminator or an analog or derivative thereof formulated for anal or vaginal delivery. In embodiments, the ribonucleoside chain terminator or analog or derivative thereof is present in an amount effective to inhibit retrovirus replication in a non-dividing cell. In embodiments, the pharmaceutical composition contains at least one additional anti-retroviral agent. In embodiments, the pharmaceutical composition contains a pharmaceutically acceptable medium suitable for topical application.

In another aspect, the invention provides condoms containing a ribonucleoside chain terminator or an analog or derivative thereof. In embodiments, the condom contains at least one additional anti-retroviral agent. In embodiments, the ribonucleoside chain terminator and/or the anti-retroviral agent(s) is incorporated into the condom or coats the condom. In embodiments, the ribonucleoside chain terminator and/or the anti-retroviral agent(s) is provided in a separate container. In related embodiments, the ribonucleoside chain terminator and/or the anti-retroviral agent(s) is applied onto the condom prior to use.

In another aspect, the invention provides kits containing a pharmaceutical composition having a ribonucleoside chain terminator or an analog or derivative thereof. In embodiments, the kit contains at least one additional anti-retroviral agent. In embodiments, the kit is used in any of the methods described herein, including the above-described aspects. In embodiments, the kit contains instructions for use.

In any of the above aspects of the invention, the non-dividing cell is a macrophage, a naive resting T cell, or a memory T cell.

In any of the above aspects of the invention, the ribonucleoside chain terminator has a nucleobase that is well-known in the art. In embodiments, the ribonucleoside chain terminator has one of the following nucleobases: adenine; guanine; uracil; cytosine; inosine; pyrazolo[3,4-d]pyrimidine; 5-methylcytosine; 5-hydroxymethyl cytosine; 2-aminoadenine; 6-methyl adenine; 6-methyl guanine; 2-propyl adenine; 2-propyl guanine; 2-thiouracil; 2-thiocytosine; 5-halouracil; 5-halocytosine; 5-propynyl uracil; 5-propynyl cytosine; 6-azo uracil; 6-azo cytosine; 5-uracil; 4-thiouracil; 8-halo adenine; 8-halo guanine; 8-amino adenine; 8-amino guanine; 8-thiol adenine; 8-thiol guanine; 8-thioalkyl adenine; 8-thioalkyl guanine; 8-hydroxyl adenine; 8-hydroxyl guanine; 5-halo uracil; 5-halo cytosine; 5-bromo uracil; 5-bromo cytosine; 5-trifluoromethyl uracil; 5-trifluoromethyl cytosine; 7-methylguanine; 7-methyladenine, 8-azaguanine; 8-azaadenine; 7-deazaguanine; 7-deazaadenine; 3-deazaguanine; 3-deazaadenine; pyrazolo[3,4-d]pyrimidine; imidazo[1,5-a]1,3,5 triazinone; 9-deazapurine; imidazo[4,5-d]pyrazine; thiazolo[4,5-d]pyrimidine; pyrazin-2-one; 1,2,4-triazine; pyridazine; or 1,3,5 triazine. In embodiments, the ribonucleoside chain terminator has one of the following nucleobases: adenine; guanine; uracil; cytosine; or inosine.

In any of the above aspects of the invention, the ribonucleoside chain terminator or analog or derivative thereof is a ribonucleotide chain terminator or analog or derivative thereof.

In any of the above aspects of the invention, the anti-retroviral agent is a nucleoside reverse transcriptase inhibitor, a nucleotide reverse transcriptase inhibitor, a non-nucleoside reverse transcriptase inhibitor, a protease inhibitor, a fusion inhibitor, or an integrase inhibitor.

In embodiments, the nucleoside reverse transcriptase inhibitor is zidovudine, didanosine, stavudine, lamivudine, abacavir, apricitabine, emtricitabine, entecavir, zalcitabine, dexelvucitabine, alovudine, amdoxovir, elvucitabine, AVX754, BCH-189, phosphazid, racivir, SP1093V, stampidine, phosphonovir, idoxuridine, or an analog or derivative thereof.

In embodiments, the nucleotide reverse transcriptase inhibitor is tenofovir, adefovir, or an analog or derivative thereof.

In embodiments, the non-nucleoside reverse transcriptase inhibitor is foscarnet, efavirenz, nevirapine, delavirdine, etravirine, or an analog or derivative thereof.

In embodiments, the protease inhibitor is invirase, fortovase, norvir, crixivan, viracept, agenerase, kaletra, reyataz, fosamprenavir, tipranavir, saquinavir, ritonavir, indinavir, nelfinavir, amprenavir, lopinavir, atazanavir, darunavir, or an analog or derivative thereof.

In embodiments, the fusion inhibitor is maraviroc, enfuvirtide, or an analog or derivative thereof.

In embodiments, integrase inhibitor is raltegravir, elvitegravir, or an analog or derivative thereof.

In any of the above aspects of the invention, the subject is a human or a non-human primate. In embodiments, the subject is human.

In any of the above aspects of the invention, the retrovirus is human immunodeficiency virus or simian immunodeficiency virus. In embodiments, the retrovirus is human immunodeficiency virus.

In any of the above aspects of the invention that involve administration of a ribonucleoside chain terminator to a subject, the ribonucleoside chain terminator is administered to the subject in a pharmaceutical composition orally, transdermally, by inhalation, or by injection.

In embodiments, the pharmaceutical composition is administered to the subject transdermally. In related embodiments, the pharmaceutical composition is in the form of a spray, gel, cream, foam, lotion, ointment, salve, powder, or suppository. In related embodiments, the pharmaceutical composition is administered to the vagina, anus, or mouth of the subject. In related embodiments, the pharmaceutical composition is coated on a condom or is incorporated into a condom. In related embodiments, the pharmaceutical composition is provided in a separate container from the condom and is applied onto the condom prior to use.

In embodiments, the pharmaceutical composition is administered to the subject orally. In related embodiments, the pharmaceutical composition is in the form of a tablet or capsule.

In any of the above aspects of the invention that involve co-administration of at least one additional anti-retroviral agent to a subject, the anti-retroviral agent is administered to the subject in a pharmaceutical composition orally, transdermally, by inhalation, or by injection. In embodiments, the anti-retroviral agent and the ribonucleoside chain terminator are administered to the subject via different routes.

In embodiments, the pharmaceutical composition is administered to the subject transdermally. In related embodiments, the pharmaceutical composition is in the form of a spray, gel, cream, foam, lotion, ointment, salve, powder, or suppository. In related embodiments, the pharmaceutical composition is administered to the vagina, anus, or mouth of the subject. In related embodiments, the pharmaceutical composition is coated on a condom or is incorporated into a condom. In related embodiments, the pharmaceutical composition is provided in a separate container from the condom and is applied onto the condom prior to use.

In embodiments, the pharmaceutical composition is administered to the subject orally. In related embodiments, the pharmaceutical composition is in the form of a tablet or capsule.

In any of the above aspects of the invention that involve administration of a pharmaceutical composition to a subject, the pharmaceutical composition contains a pharmaceutically acceptable carrier or a pharmaceutically acceptable medium suitable for topical application.

In any of the above aspects of the invention that involve use of a ribonucleoside chain terminator in combination with at least one additional anti-retroviral agent, the ribonucleoside chain terminator and the anti-retroviral agent(s) are administered simultaneously or within about 5 days of each other. In embodiments, the ribonucleoside chain terminator and the anti-retroviral agent(s) are administered simultaneously. In embodiments, the ribonucleoside chain terminator and the anti-retroviral agent(s) are administered within about 5 days of each other.

Additional objects and advantages of the invention will be set forth in part in the description which follows, and in part will be obvious from the description, or may be learned by practice of the invention. The objects and advantages of the invention will be realized and attained by means of the elements and combinations disclosed herein, including those pointed out in the appended claims. It is to be understood that both the foregoing general description and the following detailed description are exemplary and explanatory only and are not restrictive of the invention as claimed. The accompanying drawings, which are incorporated in and constitute a part of this specification, illustrate several embodiments of the invention and, together with the description, serve to explain the principles of the invention.

DEFINITIONS

To facilitate an understanding of the present invention, a number of terms and phrases are defined below.

As used herein, the singular forms "a", "an", and "the" include plural forms unless the context clearly dictates otherwise. Thus, for example, reference to "a ribonucleoside chain terminator" includes reference to more than one ribonucleoside chain terminator.

Unless specifically stated or obvious from context, as used herein, the term "or" is understood to be inclusive.

As used herein, the terms "comprises," "comprising," "containing," "having" and the like can have the meaning ascribed to them in U.S. patent law and can mean "includes," "including," and the like; "consisting essentially of" or "consists essentially" likewise has the meaning ascribed in U.S. patent law and the term is open-ended, allowing for the presence of more than that which is recited so long as basic or novel characteristics of that which is recited is not changed by the presence of more than that which is recited, but excludes prior art embodiments.

As used herein, the term "retrovirus" is inclusive of any virus that utilizes reverse transcriptase in the viral replication cycle and therefore is susceptible to the antiviral activity of nucleoside or nucleotide analogs. The term "retrovirus" is specifically inclusive of human immunodeficiency virus (HIV-1 and HIV-2) and simian immunodeficiency virus (SIV). Additional examples of retroviruses include bovine immunodeficiency virus (BIV), caprine encephalitis-arthritis virus (CAEV), equine infectious anemia virus (EIAV), feline immunodeficiency virus (FIV), goat leukoencephalitis virus (GLV), Jembrana virus (JDV), maedi/visna virus (MVV), and progressive pneumonia virus (PPV). The HIV can be type 1 (HIV-1) or type 2 (HIV-2). The HIV can be from any HIV Glade (e.g., A-G), strain or variant, including, for example, HIV-1:ARV-2/SF-2, HIV-1:BRU (LAI), HIV-1:CAM1, HIV-1:ELI, HIV-1:HXB2, HIV-1:IIIB, HIV-1:MAL, HIV-1:MN, HIV-1:NDK, HIV-1:PV22, HIV-1:RF, HIV-1:U455, and HIV-1:Z2. Also encompassed are viruses such as hepatitis B virus (HBV) that although not technically classified as retroviruses, nonetheless utilize a reverse transcriptase and are therefore susceptible to the antiviral activity of nucleoside or nucleotide analogs.

As used herein, terms such as "inhibiting retrovirus replication" or "inhibition of retrovirus replication" means any interference in, inhibition of, and/or prevention of retrovirus replication. As such, methods of inhibition of the present invention are useful in inhibiting the infectivity of a retrovirus, inhibition of reverse transcription, inhibition of viral maturation, inhibiting formation of virions, and the like.

"Infected cells," as used herein, includes cells infected naturally by membrane fusion and subsequent insertion of the viral genome into the cells, or transfection of the cells with viral genetic material through artificial means. These methods include, but are not limited to, calcium phosphate transfection, DEAE-dextran mediated transfection, microinjection, lipid-mediated transfection, electroporation, or infection.

By "inhibit" is meant a reduction in activity, level, or other measurable parameter relative to a reference (i.e., an untreated control). Such inhibition need not be complete, but can be by about 10%, 25%, 50%, 75% or more.

By "agent" is meant any small molecule chemical compound, antibody, nucleic acid molecule, or polypeptide, or fragments thereof.

"Anti-retroviral agent," as used herein, refers to any process, action, application, therapy, or the like, wherein a subject receives medical aid with the object of improving the subject's condition, directly or indirectly by inhibiting replication of a retrovirus. When "anti-retroviral agent" refers to a small molecule chemical compound, antibody, nucleic acid molecule, or polypeptide, the term "anti-retroviral agent" includes an analog or derivative thereof. Examples of anti-retroviral agents include ribonucleoside chain terminators, nucleoside reverse transcriptase inhibitors, nucleotide reverse transcriptase inhibitors, non-nucleoside reverse transcriptase inhibitors, protease inhibitors, fusion inhibitors, integrase inhibitors, and analogs or derivatives thereof.

"Ribonucleoside chain terminator," as used herein, refers to a chemical analog of a ribonucleoside that inhibits a viral reverse transcriptase or polymerase enzyme and therefore the ability of a virus to infect or replicate in a host cell. The ribonucleoside chain terminator lacks 3'-hydroxy function on the ribose moiety of the ribonucleoside. When the ribonucleoside chain terminator is covalently incorporated into a nascent DNA strand by the viral reverse transcriptase or polymerase enzyme, the lack of 3'-hydroxyl function in the ribonucleoside prevents further attachment of additional nucleotides. Ribonucleoside chain terminators therefore terminate viral DNA strand prolongation, thereby leading to inhibition of viral replication. A ribonucleoside chain terminator can be a chemical analog of a ribonucleoside or a ribonucleotide. If in the ribonucleoside form, the ribonucleoside chain terminator will be phosphorylated by host cellular kinases to produce the active triphosphate metabolite.

The term "nucleoside reverse transcriptase inhibitor" refers to a member of a class of drugs that are chemical analogs of a nucleoside that inhibit a viral reverse transcriptase or polymerase enzyme and therefore the ability of a virus to infect or replicate in a host cell. A nucleoside reverse transcriptase inhibitor is a chemical analog of a deoxyribonucleoside. Examples of nucleoside reverse transcriptase inhibitors include zidovudine (AZT), didanosine, stavudine, lamivudine, abacavir, apricitabine, emtricitabine, entecavir, zalcitabine, dexelvucitabine, alovudine, amdoxovir, elvucitabine, AVX754, BCH-189, phosphazid, racivir, SP1093V, stampidine, phosphonovir, idoxuridine, and analogs or derivatives thereof.

The term "nucleotide reverse transcriptase inhibitor" refers to a member of a class of drugs that are chemical analogs of a nucleotide that inhibit a viral reverse transcriptase or polymerase enzyme and therefore the ability of a virus to infect or replicate in a host cell. A nucleotide reverse transcriptase inhibitor is a chemical analog of a deoxyribonucleotide. Examples of nucleotide reverse transcriptase inhibitors include tenofovir, adefovir, and analogs or derivatives thereof.

The term "non-nucleoside reverse transcriptase inhibitor" refers to a class of drugs that are not chemical analogs of a nucleoside or nucleotide and that allosterically inhibit a viral reverse transcriptase or polymerase enzyme. A non-nucleoside reverse transcriptase inhibitor binds to a reverse transcriptase or a polymerase at a site distinct from the binding site of a ribonucleoside, nucleoside, or nucleotide reverse transcriptase inhibitor, e.g., the active site of the enzyme. Examples of non-nucleoside reverse transcriptase inhibitors include foscarnet, efavirenz, nevirapine, delavirdine, and etravirine, and analogs or derivatives thereof.

The term "protease inhibitor" refers to a class of drugs that are not chemical analogs of a nucleoside or nucleotide and that inhibit a viral protease. Protease inhibitors inhibit the activity of viral protease to cleave nascent proteins for final assembly of new virions. Examples of protease inhibitors include invirase, fortovase, norvir, crixivan, viracept, agenerase, kaletra, reyataz, fosamprenavir, tipranavir, saquinavir, ritonavir, indinavir, nelfinavir, amprenavir, lopinavir, atazanavir, darunavir, and analogs or derivatives thereof.

The term "fusion inhibitor" refers to a class of drugs that are not chemical analogs of a nucleoside or nucleotide and that block entry of a retroviral virion into a viral host cell. Fusion inhibitors interfere with i) the ability of a retroviral virion to bind to a viral host cell, ii) the ability of a retroviral virion to fuse with a viral host cell, or iii) entry of the viral core into a viral host cell. Examples of fusion inhibitors include maraviroc, enfuvirtide, and analogs or derivatives thereof.

The term "integrase inhibitor" refers to a class of drugs that are not chemical analogs of a nucleoside or nucleotide and that inhibit a viral integrase enzyme. Integrase inhibitors inhibit the activity of viral integrase, which is essential for integration of the viral genome into the cellular genome, thereby blocking viral replication. Examples of integrase inhibitors include raltegravir, elvitegravir, and analogs or derivatives thereof.

By "analog" is meant a molecule that is not identical, but has analogous functional or structural features. For example, an amide, ester, carbamate, carbonate, ureide, or phosphate analog of an anti-retroviral agent is a molecule that either: 1) does not destroy the biological activity of the anti-retroviral agent and confers upon that anti-retroviral agent advantageous properties in vivo, such as uptake, duration of action, or onset of action; or 2) is itself biologically inactive but is converted in vivo to a biologically active compound. Analogs include prodrug forms of an anti-retroviral agent (see Freeman and Ross in *Progress in Medicinal Chemistry* 34:112-147 (1997)). A prodrug is any compound that when administered to a biological system generates the anti-retroviral agent as a result of spontaneous chemical reaction(s), enzyme catalyzed chemical reaction(s), and/or metabolic chemical reaction(s).

The term "derivative" means a pharmaceutically active compound with equivalent or near equivalent physiological functionality to a given anti-retroviral agent. As used herein, the term "derivative" includes any pharmaceutically acceptable salt, ether, ester, prodrug, solvate, stereoisomer including enantiomer, diastereomer or stereoisomerically enriched or racemic mixture, and any other compound which upon administration to the recipient, is capable of providing (directly or indirectly) such a compound or an antivirally active metabolite or residue thereof.

A "pharmaceutically acceptable salt" of an anti-retroviral agent recited herein is an acid or base salt that is generally considered in the art to be suitable for use in contact with the tissues of human beings or animals without excessive toxicity, irritation, allergic response, or other problem or complication. Such salts include mineral and organic acid salts of basic residues such as amines, as well as alkali or organic salts of acidic residues such as carboxylic acids. Specific pharmaceutical salts include, but are not limited to, salts of acids such as hydrochloric, phosphoric, hydrobromic, malic, glycolic, fumaric, sulfuric, sulfamic, sulfanilic, formic, toluenesulfonic, methanesulfonic, benzene sulfonic, ethane disulfonic, 2-hydroxyethylsulfonic, nitric, benzoic, 2-acetoxybenzoic, citric, tartaric, lactic, stearic, salicylic, glutamic, ascorbic, pamoic, succinic, fumaric, maleic, propionic, hydroxymaleic, hydroiodic, phenylacetic, alkanoic such as acetic, HOOC—$(CH_2)_n$—COOH where n is 0-4, and the like. Similarly, pharmaceutically acceptable cations include, but are not limited to sodium, potassium, calcium, aluminum, lithium and ammonium. Those of ordinary skill in the art will recognize further pharmaceutically acceptable salts for the anti-retroviral agents provided herein, including those listed by *Remington's Pharmaceutical Sciences*, 17th ed., Mack Publishing Company, Easton, Pa., p. 1418 (1985). In general, a pharmaceutically acceptable acid or base salt can be synthesized from a parent compound that contains a basic or acidic moiety by any conventional chemical method. Briefly, such salts can be prepared by reacting the free acid or base forms of these compounds with a stoichiometric amount of the appropriate base or acid in an appropriate solvent.

As used herein, the term "nucleobase" refers to the heterocyclic nitrogenous base of a nucleoside, nucleoside analog, nucleotide, or nucleotide analog. Nucleobases useful according to the invention include, but are not limited to adenine, cytosine, guanine, uracil, and inosine. Additional nucleobases that can be comprised by a ribonucleoside chain terminator according to the invention include, but are not limited to naturally-occurring and synthetic derivatives of the preceding group, for example, pyrazolo[3,4-d]pyrimidines, 5-methylcytosine (5-me-C), 5-hydroxymethyl cytosine, 2-aminoadenine, 6-methyl and other alkyl derivatives of adenine and guanine, 2-propyl and other alkyl derivatives of adenine and guanine, 2-thiouracil, 2-thiocytosine, 5-halouracil and cytosine, 5-propynyl uracil and cytosine, 6-azo uracil and cytosine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine, 3-deazaadenine, pyrazolo[3,4-d]pyrimidine, imidazo[1,5-a]1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

Nucleobases useful according to the invention will permit a ribonucleoside, nucleosidem or nucleotide bearing that nucleobase to be enzymatically incorporated into a polynucleotide chain and will form Watson-Crick base pairs with a nucleobase on an antiparallel nucleic acid strand.

By "viral host cell" is meant a cell having or is permissive for viral infection. Exemplary viral host cells include macrophages, quiescent T cells, naive resting T cells, and memory T cells.

By "non-dividing" is meant a terminally differentiated cell or other quiescent cell type that divides rarely, if at all.

"Administering" is defined herein as a means of providing an agent or a composition containing the agent to a subject in a manner that results in the agent being inside the subject's body. Such an administration can be by any route including, without limitation, oral, transdermal (e.g., vagina, rectum, oral mucosa), by injection (e.g., subcutaneous, intravenous, parenteral, intraperitoneal, intrathecal), or by inhalation (e.g., oral or nasal). Pharmaceutical preparations are, of course, given by forms suitable for each administration route.

The term "subject" or "patient" refers to an animal which is the object of treatment, observation, or experiment. By way of example only, a subject includes, but is not limited to, a mammal, including, but not limited to, a human or a non-human mammal, such as a non-human primate, bovine, equine, canine, ovine, or feline.

As used herein, the terms "prevent," "preventing," "prevention," "prophylactic treatment," and the like, refer to reducing the probability of developing a disorder or condition in a subject, who does not have, but is at risk of or susceptible to developing a disorder or condition, e.g., viral infection.

As used herein, the terms "treat," treating," "treatment," and the like refer to reducing or ameliorating a disorder or condition, e.g., viral infection, and/or symptoms associated therewith. It will be appreciated that, although not precluded, treating a disorder or condition does not require that the disorder, condition, or symptoms associated therewith be completely eliminated.

The term "therapeutic effect" refers to some extent of relief of one or more of the symptoms of a retrovirus-related disorder. In reference to the treatment of HIV, a therapeutic effect refers to one or more of the following: 1) reduction in the number of infected cells; 2) reduction in the concentration of virions present in serum; 3) inhibiting (e.g., slowing to some extent, preferably stopping) the rate of HIV replication; 4) increasing T-cell count; 5) relieving or reducing to some extent one or more of the symptoms associated with HIV; and 6) relieving or reducing the side effects associated with the administration of other anti-retroviral agents.

"Therapeutically effective amount" is intended to qualify the amount required to achieve a therapeutic effect. A physician or veterinarian having ordinary skill in the art can readily determine and prescribe the "therapeutically effective amount" (e.g., $ED_{50}$) of the pharmaceutical composition required. For example, the physician or veterinarian could start doses of the compounds of the invention employed in a pharmaceutical composition at levels lower than that required in order to achieve the desired therapeutic effect and gradually increase the dosage until the desired effect is achieved.

Typically a therapeutically effective dosage should produce a serum concentration of compound of from about 0.1 ng/ml to about 50-100 µg/ml. The pharmaceutical compositions typically should provide a dosage of from about 0.001 mg to about 2000 mg of compound per kilogram of body weight per day. For example, dosages for systemic administration to a human patient can range from 1-10 µg/kg, 20-80 µg/kg, 5-50 µg/kg, 75-150 µg/kg, 100-500 µg/kg, 250-750 µg/kg, 500-1000 µg/kg, 1-10 mg/kg, 5-50 mg/kg, 25-75 mg/kg, 50-100 mg/kg, 100-250 mg/kg, 50-100 mg/kg, 250-500 mg/kg, 500-750 mg/kg, 750-1000 mg/kg, 1000-1500 mg/kg, 1500-2000 mg/kg, 5 mg/kg, 20 mg/kg, 50 mg/kg, 100 mg/kg, 500 mg/kg, 1000 mg/kg, 1500 mg/kg, or 2000 mg/kg. Pharmaceutical dosage unit forms are prepared to provide from about 1 mg to about 5000 mg, for example from about 100 to about 2500 mg of the compound or a combination of essential ingredients per dosage unit form.

The phrase "combination therapy" embraces the administration of a ribonucleoside chain terminator and a secondary pharmaceutical therapy (e.g., agent) as part of a specific treatment regimen intended to provide a beneficial effect from the co-action of two therapies. The beneficial effect of the combination includes, but is not limited to, pharmacokinetic or pharmacodynamic co-action resulting from the combination of therapeutic agents. Administration of these therapeutic agents in combination typically is carried out over a defined time period (usually minutes, hours, days, or weeks depending upon the combination selected). "Combination therapy" generally is not intended to encompass the administration of two or more of these therapeutic agents as part of separate monotherapy regimens that incidentally and arbitrarily result in the combinations of the present invention. "Combination therapy" is intended to embrace administration of these therapeutic agents in a sequential manner, that is, wherein each therapeutic agent is administered at a different time, as well as administration of these therapeutic agents, or at least two of the therapeutic agents, in a substantially simultaneous manner. Substantially simultaneous administration can be accomplished, for example, by administering to the subject a single capsule having a fixed ratio of each therapeutic agent or in multiple, single capsules for each of the therapeutic agents. For example, one combination of the present invention comprises a ribonucleoside chain terminator and at least one additional anti-retroviral agent at the same or different times or they can be formulated as a single, co-formulated pharmaceutical composition comprising the two compounds. As another example, a combination of the present invention a ribonucleoside chain terminator and at least one additional anti-retroviral agent formulated as separate pharmaceutical compositions that can be administered at the same or different time. Sequential or substantially simultaneous administration of each therapeutic agent can be effected by any appropriate route including, but not limited to, oral routes, intravenous routes, intramuscular routes, and direct absorption through mucous membrane tissues (e.g., nasal, mouth, vaginal, and rectal). The therapeutic agents can be administered by the same route or by different routes. For example, one component of a particular combination may be administered by intravenous injection while the other component(s) of the combination may be administered orally. The components may be administered in any therapeutically effective sequence.

The phrase "combination" embraces groups of compounds or non-drug therapies useful as part of a combination therapy.

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein are modified by the term about.

The recitation of a listing of chemical groups in any definition of a variable herein includes definitions of that variable as any single group or combination of listed groups. The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

DESCRIPTION OF THE DRAWINGS

FIG. 3A is a graph comparing the ratios of rNTP and dNTP concentrations in human primary macrophages and activated PMBCs (see Table 1). The calculated fold differences of the dNTP and rNTP concentration disparity in macrophages and activated PBMCs are marked for each of the four rNTP and dNTP pairs. FIG. 3B includes a gel. A 23mer DNA primer (P) annealed to an RNA 40mer template (T) (10 nM T/P complex) was extended by HIV-1 RT (green circle, 200 nM) at macrophage (M) and PBMC (PB) dNTP and rNTP concentrations (see Table 1) in the presence of α-$^{32}$P-UTP at a 1/690 ratio to nonradioactive UTP. The reactions were terminated by 10 mM EDTA, and reaction products were inactivated at 95° C. for 3 minutes, purified with a Qiagen nucleotide removal column, and mixed with an equal amount of the 23-mer 5' end $^{32}$P labeled DNA primer as a loading control (LC) before application onto 15% polyacrylamide denaturing gels (left panel). The fully extended product density (F) in the macrophage and T cell nucleotide reactions were quantified and compared. Results were normalized with the loading control (LC) when calculating the fold difference of the rNTP incorporation between macrophages and T cell nucleotide pools (right panel). FIG. 3C includes a gel. Time-course DNA synthesis by HIV-1 RT (20 nM) with a 5' end $^{32}$P-labeled 17-mer primer (P) annealed to an RNA 40mer template (T) (2 nM T/P) at the macrophage dNTP concentration (see Table 1) for 2, 4, 8, 16, and 20 minutes in the presence and absence of macrophage rNTP pools (see Table 1). C: no RT control. F: fully extended product, and P: unextended primer. FIG. 3D includes a gel. Reactions were conducted under the identical reaction condition described for FIG. 3B except that these reactions used 5' end $^{32}$P-labeled primer. In addition, these reactions did not include α-$^{32}$P-UTP. F: full length product, P: unextended product, M: macrophages, PB: PBMCs, and C: no RT control. FIG. 3E includes a gel. Reactions were conducted under the identical reaction condition described for FIG. 3C except that the reactions used a 40-mer DNA template. F: full length product, P: unextended product, and C: no RT control.

FIG. 4A is a gel showing a representative time-course reaction set for dATP alone, ATP alone, or both dATP and ATP at their macrophage concentrations. P: unextended 17-mer primer, E: extended 18-mer product. and C: no RT control. FIG. 4B includes graphs. The percentages of the primer extension at early time points were plotted to compare the incorporation rate for each dNTP or rNTP alone as well as for dNTPs and rNTPs at their macrophage concentrations. FIG. 4C is a gel showing a time-course reaction. Identical reactions were conducted with SIVagm Sab-1 RT. FIG. 4D is a table showing the steady state $K_m$ values of HIV-1 RT to rNTPs determined by single nucleotide incorporation assays. FIG. 4E is a graph comparing rNTP concentrations (black bars) of macrophages and PBMCs and the $K_m$ values (red zone) of HIV-1 RT to rNTPs. Grey bars: average concentrations of dNTPs of the two target cell types obtained from Table 1.

FIG. 5A is a gel showing the reaction products of single nucleotide (dATP) extension with dTTP for the first nucleotide incorporation with HIV-1 RT (green circle, 40 nM). FIG. 5B is a gel showing the reaction products of dATP and dGTP extension for the first and second dNTP incorporations at their macrophage concentrations (see Table 1), respectively, from the 3' end-dCMP or rCMP primers. The reactions in FIGS. 5A and 5B were conducted for 30, 60, 90, 120, 240, 480, and 720 seconds. P: unextended primer, E1: one nucleotide extended product, E2: two nucleotide extended products, and C: no RT control.

FIG. 6A includes a graph showing the cytotoxicity of rACT in human primary CD4+ T cells, U937 cells, and CHME5 cells. These three types of cells were cultured and treated with different concentrations of rACT (up to 1 mM) for 2 days, and the percentage of live and dead cells were determined by FACS and/or trypan blue staining. The percentage of the live cells in the absence of rACT was used for normalization (100%), and the base line cell death of these cell types in the absence of rACT were less than 5%. FIG. 6B includes FACS results. Human primary macrophages were preincubated with different concentrations of rACT (0, 10, 100 and 100 µM) for 24 hours and then transduced with HIV-GFP vector (equal p24 amounts). The percentages of GFP positive macrophages and PI positive cells in a representative donor, which were determined by FACS at 7 days post transduction, are shown. FIG. 6C is a graph showing the percentages of the GFP positive macrophages in three donors. FIG. 6D includes a graph showing the copy number of HIV-1 2LTR DNA circles in transduced macrophages. Genomic DNAs were extracted from the transduced macrophages in FIG. 6B, and were used in a quantitative 2LTR circle PCR assay. Viral production was determined by p24 ELISA with the collected media. These experiments were performed in triplicate from three different blood donors. FIG. 6E is a graph showing the percentages of the GFP positive activated CD4+ T cells from two donors. Transduction and drug treatment were conducted identically except the infection duration was 2 days.

FIG. 7A includes a graph. The dUTP concentrations of macrophages and activated PBMCs as determined by LC-MS/MS (summarized in Table 1) were plotted with grey bars. The black bars represent dTTP concentrations of human primary macrophages and activated CD4+ T cells as shown above in FIG. 1. FIG. 7B includes a graph showing the dUTP/dTTP concentration ratios calculated from LC-MS/MS analysis.

FIG. 8A includes a schematic of a coupled RT extension reaction UNG2 digestion assay and a gel. RT was incubated with i) the dNTP concentrations found in macrophages or PBMCs, and ii) either the dUTP concentration for those cells types or ddH$_2$0. These reactions were quenched with EDTA and subjected to E. Coli UNG2 digestion, followed by 95° C. incubation and UREA PAGE gel electrophoresis. The digested bands (*) were quantified and plotted relative to total unextended and extended products. FIG. 8B shows these results in a graph. FIG. 8C includes a gel showing the results of single nucleotide extension reactions of HIV-1 RT with dTTP and dUTP concentrations found in macrophages. FIG. 8D shows these results in a graph. The rates of product formation for dTTP (black line), dUTP (blue line), and both dTTP and dUTP (green line) were plotted.

FIG. 9A is a gel containing the SIV$_{Sab1}$ RT assay products. FIG. 9B is a gel containing the FIV RT assay products. FIG. 9C is a gel containing the Foamy Virus RT assay products. FIG. 9D is a gel containing the MuLV RT assay products.

FIG. 10A includes images of transduced cells imaged for brightfield and GFP. Percent transduction is represented above the images and the drug concentration is represented below. FIG. 10B is a graph showing the results from flow cytometry analysis of the transduced cells.

FIGS. 11A-11D are graphs showing viral production in macrophages treated with rACT, rCCT, rGCT, and rUCT, respectively.

FIG. 12 includes a graph of cell survival rate with each rNCTP. The results demonstrate that no significant cytotoxicity was observed for the rNCTPs during macrophage culture.

DETAILED DESCRIPTION OF THE INVENTION

Figure 1:
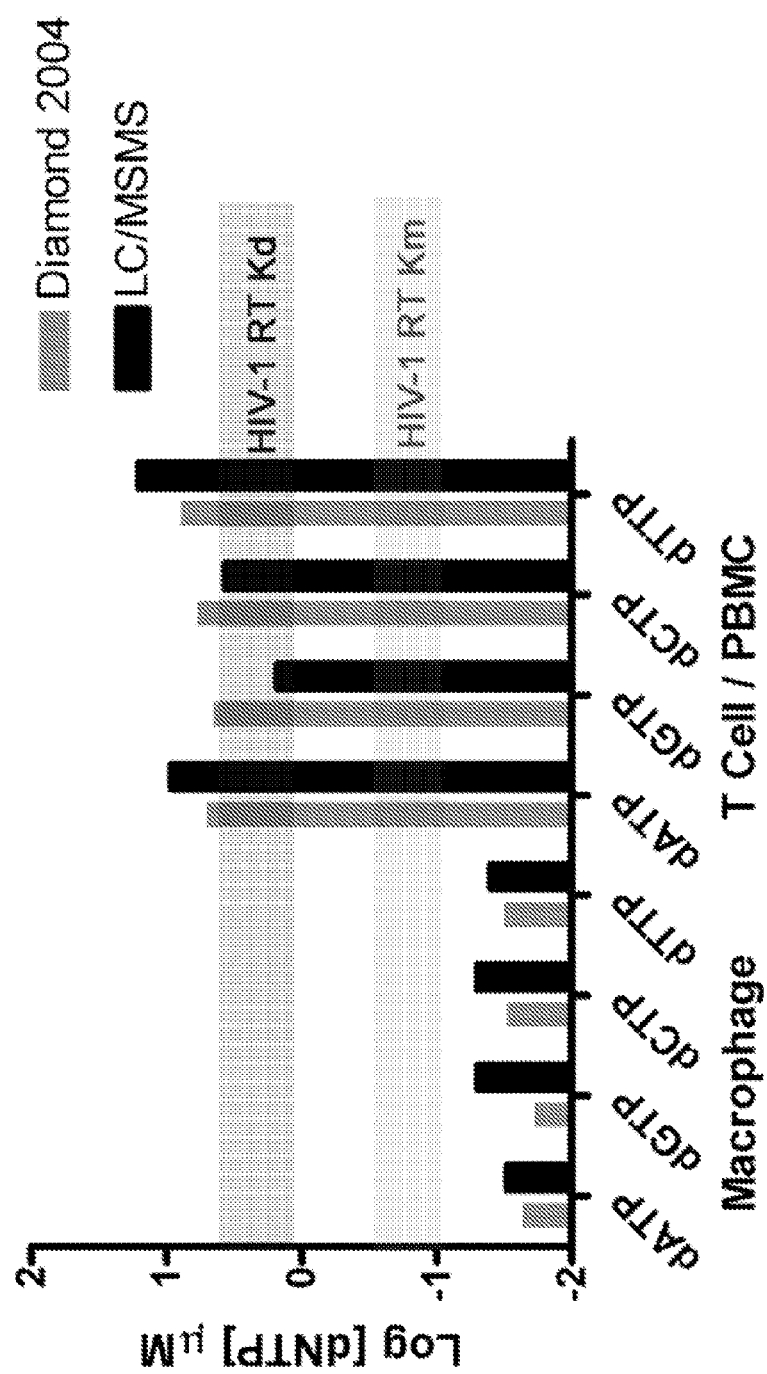
FIG. 1 is a graph showing a comparison of dNTP concentrations of human primary macrophages and activated PBMCs. The dNTP concentrations of macrophages and activated PBMCs, which were determined by LC-MS/MS and summarized in Table 1, were plotted with black bars. The grey bars represent dNTP concentrations of human primary macrophages and activated CD4+ T cells previously determined by an enzyme-based dNTP assay. The red and blue zones represent the ranges of previously determined steady state $K_m$ and pre-steady state $K_d$ values of HIV-1 RT to dNTP substrates, respectively.

The invention features methods, compositions, and kits that are useful for inhibiting retrovirus infection.

The invention is based, at least in part, on the discovery that ribonucleotide triphosphates (rNTPs), which are normally the substrates of RNA polymerases, are used as substrates by viral reverse transcriptase under conditions found in non-dividing cells (e.g., macrophages). Specifically, biochemical simulation of viral reverse transcription revealed that rNTPs are efficiently incorporated into DNA in a non-dividing cell, but not in a dividing cell environment. Consistent with these biochemical findings, it has been discovered that ribonucleoside chain terminators (rNCTs) inhibit proviral DNA synthesis in non-dividing cells more efficiently than in dividing cells. These findings reveal that the biochemical landscape of retroviral replication in non-dividing cells is unique and that ribonucleoside chain terminators provide a new class of antiretroviral agents that can specifically target retroviral infection of non-dividing cells (e.g., macrophages, naive resting T cells, memory T cells). Accordingly, the invention provides rNCTs that prevent the establishment and persistence of reservoirs of virus infection in vivo, particularly of retroviruses (e.g., HIV) that replicate in non-dividing viral host cells. The invention also relates to combination therapies including rNCTs.

Ribonucleoside Chain Terminators

In general, the invention includes ribonucleoside chain terminators (rNCTs) that inhibit the activity of viral reverse transcriptase or polymerase enzyme. The rNCT can be any chemical analog of a ribonucleoside that terminates viral DNA strand prolongation. The rNCT serves as a substrate for a viral reverse transcriptase or polymerase enzyme, but once incorporated onto the end of a growing polynucleotide chain, the rNCT cannot itself serve as a substrate for the attachment of subsequent nucleotide residues.

Suitable rNCTs for use in the invention are well-known in the art. For example, rNCTs can be chemical analogs of a ribonucleoside that lacks 3'-hydroxyl function on the ribose moiety of the ribonucleoside, e.g., 3' deoxyribonucleosides. These rNCTs may comprise any one of the following nucleobases: adenine, cytosine, guanine, uracil, and inosine. In addition, rNCTs of the invention may include naturally-occurring and synthetic derivatives of the preceding nuclebases, for example, pyrazolo[3,4-d]pyrimidines, 5-methylcytosine (5-me-C), 5-hydroxymethyl cytosine, 2-aminoadenine, 6-methyl and other alkyl derivatives of adenine and guanine, 2-propyl and other alkyl derivatives of adenine and guanine, 2-thiouracil, 2-thiocytosine, 5-halouracil and cytosine, 5-propynyl uracil and cytosine, 6-azo uracil and cytosine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 8-azaguanine and 8-azaadenine, 7-deazaguanine and 7-deazaadenine and 3-deazaguanine, 3-deazaadenine, pyrazolo[3,4-d]pyrimidine, imidazo[1,5-a] 1,3,5 triazinones, 9-deazapurines, imidazo[4,5-d]pyrazines, thiazolo[4,5-d]pyrimidines, pyrazin-2-ones, 1,2,4-triazine, pyridazine; and 1,3,5 triazine.

Methods for making rNCTs are well-known in the art and assays for testing rNCTs are well-known in the art, including the primer extension assays described in detail herein.

rNCTs can be in their pharmacologically inactive form and may require phosphorylation by host cellular kinases to produce the active triphosphate metabolite. rNCTs can also be in their pharmacologically active triphosphate form.

rNCTs further include analogs and derivatives of the rNCTs. For example, an rNCT can be an amide, ester, carbamate, carbonate, ureide, phosphate analog of the rNCT. The analog does not destroy the biological activity of the rNCT, and preferably confers upon the rNCT advantageous properties in vivo, such as uptake, duration of action, or onset of action. Another example is a prodrug of an rNCT. The prodrug is itself biologically inactive, but is converted in vivo to the biologically active form of the rNCT.

rNCTs derivatives include pharmaceutically acceptable salts of the rNCTs. The rNCT derivative has equivalent or near equivalent physiological functionality to the rNCT. The derivative may confer upon the rNCT advantageous properties such as improved storage stability or enhanced solubility.

Methods of Treatment

As rNCTs inhibit retroviral replication and retroviral reverse transcription in the dNTP/rNTP environment associated with non-dividing cells, rNCTs are a new class of antiretroviral agents that can specifically target retroviral infection of non-dividing cells.

The invention includes methods for inhibiting retrovirus replication in a non-dividing viral host cell. In embodiments, the method comprises contacting a non-dividing cell having or at risk of developing a retroviral infection with an rNCT. In embodiments, the retrovirus is human immunodeficiency virus.

The invention also includes methods for inhibiting retrovirus replication in a macrophage. In embodiments, the method comprises contacting a macrophage having or at risk of developing a viral infection with an rNCT. In embodiments, the retrovirus is human immunodeficiency virus.

The invention also includes methods for inhibiting the establishment or persistence of a retrovirus reservoir in a non-dividing viral host cell. In embodiments, the method comprises contacting a non-dividing cell having or at risk of developing a viral infection with an rNCT. In embodiments, the retrovirus is human immunodeficiency virus.

When the rNCT is administered to a subject, the rNCT will likely be administered as a composition in combination with a pharmaceutically acceptable carrier or excipient. Pharmaceutically acceptable carriers are physiologically acceptable and retain the therapeutic properties of the small molecules, antibodies, nucleic acids, or peptides present in the composition. Pharmaceutically acceptable carriers are well-known in the art and generally described in, for example, Remington's Pharmaceutical Sciences (18$^{th}$ Edition, ed. A. Gennaro, Mack Publishing Co., Easton, Pa., 1990). Suitable dose ranges and cell toxicity levels may be assessed using standard dose range experiments that are well-known in the art. Actual dosages administered may vary depending, for example, on the nature of the disorder, e.g., stage of virus-mediated pathology, the age, weight and health of the individual, as well as other factors.

In embodiments, rNCTs are formulated into preparations in solid, semi-solid, liquid or gaseous forms, such as tablets, capsules, pills, powders, granules, dragees, gels, slurries, ointments, solutions, suppositories, injections, inhalants and aerosols. Administration of such formulations can be achieved in various ways, including oral, buccal, parenteral, injection, intravenous, intradermal (e.g., subcutaneous, intramuscular), topical, transdermal, transmucosal, inhalation, nasal, rectal, vaginal, etc., administration. Moreover, rNCTs can be administered in a local rather than systemic manner, for example, in a depot or sustained release formulation.

For oral administration, the rNCT can be readily formulated by combining with pharmaceutically acceptable carriers that are well-known in the art. Such carriers enable the compounds to be formulated as tablets, pills, dragees, capsules, emulsions, lipophilic and hydrophilic suspensions, liquids, gels, syrups, slurries, suspensions, and the like, for oral ingestion by a subject to be treated. Pharmaceutical preparations for oral use can be obtained by mixing the rNCT with a solid excipient, optionally grinding a resulting mixture, and processing the mixture of granules, after adding suitable auxiliaries, if desired, to obtain tablets or dragee cores. Suitable excipients are, in particular, fillers such as sugars, including lactose, sucrose, mannitol, or sorbitol; and cellulose preparations such as, for example, maize starch, wheat starch, rice starch, potato starch, gelatin, gum tragacanth, methyl cellulose, hydroxypropylmethyl-cellulose, sodium carboxymethylcellulose, and/or polyvinylpyrrolidone (PVP). If desired, disintegrating agents can be added, such as a cross-linked polyvinyl pyrrolidone, agar, or alginic acid or a salt thereof such as sodium alginate.

Oral rNCT formulations can be sustained or extended-release formulations. Methods and ingredients for making sustained or extended-release formulations are well-known in the art. For example, sustained or extended-release formulations can be prepared using natural ingredients, such as minerals, including titanium dioxide, silicon dioxide; zinc oxide, and clay (see U.S. Pat. No. 6,638,521). Exemplified extended release formulations that can be used in delivering rNCT include those described in U.S. Pat. Nos. 6,635,680; 6,624,200; 6,613,361; 6,613,358, 6,596,308; 6,589,563; 6,562,375; 6,548,084; 6,541,020; 6,537,579; 6,528,080; and 6,524,621. Controlled release formulations that can be used in delivering rNCT include those described in U.S. Pat. Nos. 6,607,751; 6,599,529; 6,569,463; 6,565,883; 6,482,440; 6,403,597; 6,319,919; 6,150,354; 6,080,736; 5,672,356; 5,472,704; 5,445,829; 5,312,817; and 5,296,483. Those skilled in the art will readily recognize other applicable sustained release formulations.

rNCT can also be formulated for parenteral administration by injection, e.g., by bolus injection or continuous infusion. For injection, rNCTs can be formulated in combination with a carrier that is well-known in the art. The carriers may include distilled water; sodium chloride solutions; mixtures of sodium chloride and inorganic salts or their similar mixtures; solutions of materials such as mannitol, lactose, dextran, and glucose; amino acid solutions such as glycine and arginine; mixtures of organic acid solutions or salt solutions and glucose solutions; and other similar solutions. The injection liquid may be prepared in the form of a solution, suspension, or colloidal solution by adding an osmotic modulator; a pH controller; vegetable oil such as sesame oil or bean oil; synthetic aliphatic acid glyceride, esters of higher aliphatic acids or propylene glycol; lecithin; surfactant such as non-ionic surfactant; and conventional additives such as solubilizers, suspending agents, emulsifying agents, stabilizers, and preservatives. Formulations for injection can be presented in unit dosage form, e.g., in ampoules or in multi-dose containers. The injection may be prepared in the form of powder or lyophilization and then dissolved in the form of solution.

Another long-acting rNCT formulation is a depot preparation, which can be administered by implantation, e.g., subcutaneously or intramuscularly, or by intramuscular injection. In a depot preparation, rNCTs can be formulated with suitable polymeric or hydrophobic materials, e.g., as an emulsion in an acceptable oil, ion exchange resins, or as sparingly soluble derivatives, e.g., as a sparingly soluble salt. Methods and formulations for such depot preparations are well-known in the art.

Other parenteral routes may also be used, such as, inhalation of an rNCT formulation particularly for delivery to lungs or bronchial tissues, throat, or mucous membranes of the nose. Inhalable preparations include inhalable powders, propellant-containing metered dose aerosols, or propellant-free inhalable solutions. Inhalable preparations that can be used in delivering rNCTs are well-known in the art, for example, those inhalable preparations described in U.S. Pat. No. 7,867,987.

rNCT can also be formulated for transmucosal and transdermal administration. For transmucosal and transdermal administration, e.g., topical administration, rNCTs are formulated into a spray, gel, cream, foam, lotion, ointment, salve, powder, or suppository. Penetrants appropriate to the barrier to be permeated are used in the formulation. For example, the transmucosal and transdermal delivery agent can be, for example, DMSO, urea, 1-methyl-2-pyrrolidone, oleic acid, or a terpene (e.g., l-menthol, d-limonene, RS-(+/−)-beta-citronellol, geraniol). Further percutaneous penetration enhancers are described, for example, in *Percutaneous Penetration Enhancers*, Smith and Maibach, eds., 2nd edition, 2005, CRC Press. Exemplified transmucosal and transdermal delivery formulations that can be used in delivering rNCT include those described in U.S. Pat. Nos. 6,589,549; 6,544,548; 6,517,864; 6,512,010; 6,465,006; 6,379,696; 6,312,717; and 6,310,177.

rNCT may be applied to the vagina in any conventional manner, including aerosols, foams, jellies, creams, suppositories, tablets, tampons, etc. Compositions suitable for application to the vagina are disclosed in U.S. Pat. Nos. 2,149,240; 2,330,846; 2,436,184; 2,467,884; 2,541,103; 2,623,839; 2,623,841; 3,062,715; 3,067,743; 3,108,043; 3,174,900; 3,244,589; 4,093,730; 4,187,286; 4,283,325; 4,321,277; 4,368,186; 4,371,518; 4,389,330; 4,415,585; and 4,551,148. The present invention may be carried out by applying rNCT to the vagina in the form of such a composition. Suitable devices for applying rNCTs to the vagina are disclosed in U.S. Pat. Nos. 3,826,828; 4,108,309; 4,360,013; and 4,589,880.

rNCT may be applied to the anus in any conventional manner, including a foam, cream, jelly, etc., such as those described above with regard to vaginal application. In the case of anal application, it may be preferred to use an applicator that distributes the composition substantially evenly throughout the anus. For example, a suitable applicator is a tube 2.5 to 25 cm, preferably 5 to 10 cm, in length having holes distributed regularly along its length.

Also included in the invention are rNCT formulations for vaginal or anal administration with a solid carrier. These formulations may be presented as unit dose suppositories. Suitable carriers include cocoa butter and other materials well-known in the art. The suppositories may be conveniently formed by admixture of the rNCT with the softened or melted carrier(s) followed by chilling and shaping in moulds.

In embodiments of the invention, the rNCT formulation is topically applied to the vagina or anus to prevent HIV infection as a result of vaginal or anal intercourse. Topical application is carried out prior to the beginning of intercourse, for example 0 to 60 minutes, 0 to 30 minutes, and 0 to 5 minutes.

In embodiments of the invention, rNCTs are released from an article when the article is placed on an appropriate body part or in an appropriate body cavity. For example, the invention includes IUDs, vaginal diaphragms, vaginal sponges, pessaries, or condoms that contain or are associated with (e.g., coated) an rNCT.

In embodiments of the invention, an IUD contains or is associated with one or more rNCTs. Suitable IUDs are disclosed in U.S. Pat. Nos. 3,888,975 and 4,283,325. In embodiments of the invention, an intravaginal sponge contains or is associated with one or more rNCTs. In related embodiments, the intravaginal sponge releases the rNCTs in a time-controlled fashion. Intravaginal sponges are disclosed in U.S. Pat. Nos. 3,916,898 and 4,360,013. In embodiments of the invention, a vaginal dispenser contains or is associated with one or more rNCTs. Vaginal dispensers are disclosed in U.S. Pat. No. 4,961,931.

In embodiments, a condom contains or is associated with one or more rNCTs. In related embodiments, the rNCT is incorporated into the condom. In related embodiments, the condom is coated with an rNCT. In related embodiments, the rNCT is provided in a separate container, e.g., a package, and can be applied onto (e.g., outside and inside) the condom before the condom is used. In related embodiments, the condom is coated with a lubricant or penetration enhancing agent that comprises an rNCT. Lubricants and penetration enhancing agents are described in U.S. Pat. Nos. 4,537,776; 4,552,872; 4,557,934; 4,130,667, 3,989,816; 4,017,641; 4,954,487; 5,208,031; and 4,499,154.

rNCT formulations suitable for topical administration in the mouth include lozenges comprising the rNCT in a flavored base, usually sucrose and acacia or tragacanth; pastilles comprising the rNCT in an inert base such as gelatin and glycerin, or sucrose and acacia; and mouthwashes comprising the rNCT in a suitable liquid carrier. In embodiments of the invention, rNCT is administered in the form of a mouthwash or gargle to prevent infection during dental procedures. The mouthwash or gargle is applied just prior to the beginning of the dental procedure and optionally periodically throughout the procedure.

The amount of the pharmaceutical composition administered will, of course, be dependent on the subject being treated, on the subject's weight, the severity of the disorder, e.g., stage of virus-mediated pathology, the manner of administration, and the judgment of the prescribing physician. Determination of an effective amount is well within the capability of those skilled in the art, especially in light of the detailed disclosure provided herein. Generally, an efficacious or effective amount of a rNCT is determined by first administering a low dose of the rNCT and then incrementally increasing the administered dose or dosages until a desired effect of reduced viral titer is observed in the treated subject, with minimal or acceptable toxic side effects. Applicable methods for determining an appropriate dose and dosing schedule for administration of a pharmaceutical composition of the present invention are described, for example, in *Goodman and Gilman's The Pharmacological Basis of Therapeutics*, Goodman et al., eds., 11th Edition, McGraw-Hill 2005, and *Remington: The Science and Practice of Pharmacy*, 20th and 21st Editions, Gennaro and University of the Sciences in Philadelphia, Eds., Lippencott Williams & Wilkins (2003 and 2005).

Combination Therapies

The invention also provides methods of treating a subject using a combination treatment. rNCTs are administered near simultaneously or sequentially with at least one anti-retroviral agent. An anti-retroviral agent includes an agent that inhibits retrovirus replication. In embodiments, the anti-retroviral agent includes a nucleoside reverse transcriptase inhibitor, a nucleotide reverse transcriptase inhibitor, a non-nucleoside reverse transcriptase inhibitor, a protease inhibitor, a fusion inhibitor, or an integrase inhibitor.

In embodiments, an rNCT is administered in combination with one or more nucleoside reverse transcriptase inhibitors, including zidovudine (AZT), didanosine, stavudine, lamivudine, abacavir, apricitabine, emtricitabine, entecavir, zalcitabine, dexelvucitabine, alovudine, amdoxovir, elvucitabine, AVX754, BCH-189, phosphazid, racivir, SP1093V, stampidine, phosphonovir, idoxuridine.

In embodiments, an rNCT is administered in combination with one or more nucleotide reverse transcriptase inhibitors, including tenofovir and adefovir.

In embodiments, an rNCT is administered in combination with one or more non-nucleoside reverse transcriptase inhibitors, including foscarnet, efavirenz, nevirapine, delavirdine, and etravirine.

In embodiments, an rNCT is administered in combination with one or more protease inhibitors, including invirase, fortovase, norvir, crixivan, viracept, agenerase, kaletra, reyataz, fosamprenavir, tipranavir, saquinavir, ritonavir, indinavir, nelfinavir, amprenavir, lopinavir, atazanavir, and darunavir.

In embodiments, an rNCT is administered in combination with one or more fusion inhibitors, including maraviroc and enfuvirtide.

In embodiments, an rNCT is administered in combination with one or more integrase inhibitors, including raltegravir and elvitegravir.

The one or more nucleoside reverse transcriptase inhibitors, nucleotide reverse transcriptase inhibitors, non-nucleoside reverse transcriptase inhibitors, protease inhibitors, fusion inhibitors, and integrase inhibitors can be administered in doses according to those approved by the FDA, although the doses can be less. Approved doses for these inhibitors can be found, for example, in the FDA Orange Book, available on the worldwide web at fda.gov/cder/ob/default.htm. The rNCTs and the one or more anti-retroviral agents can be administered concurrently or independently, one, two, three, four or more times in a 24-hour period, as needed. The rNCTs and the one or more anti-retroviral agents can also be administered sequentially within about 5 days of each other.

The additional anti-retroviral agents can be formulated and administered as described above for rNCTs. In embodiments, the anti-retroviral agent(s) and the rNCT(s) are in the same pharmaceutical composition. In embodiments, the anti-retroviral agent(s) and the rNCT(s) are in separate pharmaceutical compositions.

Generally, an efficacious or effective amount of an rNCT and an additional anti-retroviral agent is determined by first administering a low dose of one or both active agents and then incrementally increasing the administered dose or dosages until a desired effect of reduced viral titer is observed in the treated subject, with minimal or no toxic side effects. Applicable methods for determining an appropriate dose and dosing schedule for administration of a combination of the present invention are described, for example, in *Goodman and Gilman's The Pharmacological Basis of Therapeutics*, 11th Edition., supra, and in *Remington: The Science and Practice of Pharmacy*, 20th and 21st Editions, supra.

Kits

The invention also provides for a pharmaceutical pack or kit for inhibiting retroviral replication. In embodiments, the kit comprises an rNCT as described herein. In embodiments, the kit comprises one or more containers filled with one or more of the ingredients of an rNCT formulation. In embodiments, the kit further comprises one or more containers filled with one or more of the ingredients of an additional anti-retroviral formulation. In embodiments, the kit comprises two containers, one containing an rNCT and the other containing at least one additional anti-retroviral agent. Associated with such container(s) can be a notice in the form prescribed by a governmental agency regulating the manufacture, use, or sale of pharmaceuticals or biological products, which notice reflects approval by the agency of manufacture, use or sale of the kit and the components therein for human administration.

In embodiments, the kit comprises instructions for using a ribonucleoside chain terminator to inhibit retrovirus replication using any of the methods described herein. In embodiments, the kit comprises instructions for using a ribonucleoside chain terminator in combination with at least one additional anti-retroviral agent to inhibit retrovirus replication using any of the methods described herein The invention also provides that the rNCT formulation be packaged in a hermetically sealed container such as an ampoule or sachette indicating the quantity of composition. In embodiments, an rNCT composition is supplied as a liquid. In other embodiments, an rNCT composition is supplied as a dry sterilized lyophilized powder or water free concentrate in a hermetically sealed container and can be reconstituted, e.g., with water or saline, to the appropriate concentration for administration to a subject.

In the above aspects and embodiments of the invention, the retrovirus can be human immunodeficiency virus.

EXAMPLES

It should be appreciated that the invention should not be construed to be limited to the examples that are now described; rather, the invention should be construed to include any and all applications provided herein and all equivalent variations within the skill of the ordinary artisan.

Example 1 dNTP and rNTP Concentrations in Primary Retrovirus Target Cell Types

Liquid chromatography-tandem mass spectrometry (LC-MS/MS) was employed to measure dNTP and rNTP pools in human primary macrophages and activated human PBMCs. These two cell types were isolated from buffy coats of healthy donors. Known amounts of $^{13}C/^{15}N$-labeled individual standards were used to determine dNTP and rNTP quantities in the samples with LC-MS/MS, and the cellular nucleotide concentrations were calculated using their cell volumes as previously reported in Diamond et al. *J. Biol. Chem.* 279: 51545-51553 (2004). The results are shown below in Table 1.

TABLE 1

Intracellular dNTP and rNTP concentrations of primary human monocyte derived macrophages and activated PBMCs as determined by LC-MS/MS.

|  | dCTP | dGTP | dATP | TTP |
|---|---|---|---|---|
|  | Concentration (µM) | | | |
| Activated PBMC | 3.67 ± 2.65 | 1.52 ± 1.01 | 9.22 ± 4.5 | 16.0 ± 5.25 |
| Macrophages (fold difference) | 0.07 ± 0.05 (1/52) | 0.07 ± 0.05 (1/22) | 0.04 ± 0.03 (1/231) | 0.05 ± 0.04 (1/320) |
|  | Amount (pmol/10$^6$ cells) | | | |
| Activated PBMC | 1.17 ± 0.85 | 0.49 ± 0.32 | 2.95 ± 1.46 | 4.85 ± 1.56 |
| Macrophages | 0.19 ± 0.13 | 0.18 ± 0.13 | 0.10 ± 0.07 | 0.13 ± 0.10 |
|  | CTP | GTP | ATP | UTP |
|  | Concentration (µM) | | | |
| Activated PBMC | 182 ± 24 | 1,745 ± 128 | 6,719 ± 560 | 690 ± 100 |

TABLE 1-continued

Intracellular dNTP and rNTP concentrations of primary human monocyte derived macrophages and activated PBMCs as determined by LC-MS/MS.

| Macrophages (fold difference) | 25 ± 8 (1/7) | 323 ± 95 (1/3) | 1,124 ± 339 (1/6) | 173 ± 47 (1/4) |
|---|---|---|---|---|
| Amount (pmol/10⁶ cells) | | | | |
| Activated PBMC | 58 ± 8 | 558 ± 41 | 2,150 ± 179 | 221 ± 32 |
| Macrosphages | 66 ± 21 | 859 ± 253 | 2,990 ± 902 | 460 ± 124 |

Macrophages were found to harbor a much lower dNTP concentration (40 nM-70 nM) than activated PBMCs (1.52-16.0 μM) (Table 1 and FIG. 1). The dNTP concentrations of macrophages and activated PBMCs determined by LC-MS/MS were very similar to previous measurements as determined by enzyme-based assays ((Diamond et al. *J. Biol. Chem.* 279:51545-51553 (2004); and Perez-Bercoff et al. *J. Virol.* 81:4540-4550 (2007)). The exception was macrophage dGTP concentration, which was 3 fold higher in the MS/MS assay than the enzyme-based assay. In the LC-MS/MS assay, the dNTP concentration in macrophages was 22-320 fold lower than in activated T cells. In contrast, as shown in Table 1, the rNTP concentration in macrophages was only 4-7 fold lower than that in activated PBMCs, indicating that non-dividing cells still maintain high rNTP concentrations, presumably due to the multiple roles of rNTPs in various cellular events such as transcription, cell signaling, and cellular metabolism, which also occur in non-dividing cells.

FIG. 1 also shows the steady state and pre-steady state kinetic parameters of HIV-1 RT. The $K_m$ values (Diamond et al. *J. Biol. Chem.* 279:51545-51553 (2004); Kopp et al., *Nucleic Acids Res.* 19:3035-3039 (1991); Preston et al., *Science* 242:1168-1171 (1988); and Wainberg et al. *Science* 271:1282-1285 (1996)), which are the dNTP concentrations giving 50% of the maximum reaction rate, are in the red zone, and the $K_d$ values (Weiss et al., *Biochemistry* 43:4490-4500 (2004); Kati et al., *J. Biol. Chem.* 267:25988-25997 (1992); Reardon, J. E., *Biochemistry* 31:4473-4479 (1992)), which indicate the dNTP binding affinity, are in the blue zone. The T cell dNTP concentrations were generally higher than the published $K_m$ and $K_d$ values of HIV-1 RT. In contrast, the macrophage dNTP concentrations were considerably lower than the $K_m$ and $K_d$ values of HIV-1 RT. Without wishing to be bound by theory, these results taken together indicate that viral DNA synthesis is relatively restricted by dNTP availability in non-dividing cells, e.g., macrophages, most likely due to suboptimal substrate binding.

Example 2

DNA Synthesis Profiles of Retrovirus RT in Cellular dNTP Pools

The dNTP concentration-dependent DNA synthesis profile of retrovirus RT was investigated in the presence of dNTP pools simulating the cellular microenvironments described in FIG. 1. A time course primer extension reaction was employed. Briefly, HIV-1 RT (green circle in FIG. 2) was incubated with i) a 19-mer 5' $^{32}$P-labeled DNA primer ("P") annealed to an RNA template encoding a 184-nt portion of the HIV-1 gag gene ("T"), and ii) dNTPs at a concentration that simulated T cell dNTP pools (1x: dATP, 23 nM; dGTP, 20 nM; dCTP, 30 nM; TTP, 32 nM) (Diamond et al. *J. Biol. Chem.* 279:51545-51553 (2004)) or dNTPs at 1/4x, 1/8x, and 1/16x of this concentration (the dNTP concentration in the 1/16x dilution is still higher than that of macrophages). As assessed by the amount of the 184-bp full length products (F in FIG. 2), DNA synthesis proceeded more slowly in the diluted/low dNTP pools as compared with the simulated T cell dNTP pool. This kinetic delay resulted in increasing early pausing by RT (see * in FIG. 2). Since the macrophage dNTP pool is an additional 2-20 times lower in concentration than even the 1/16 dilution of the simulated T cell dNTP pool, viral DNA synthesis in the macrophage environment will be kinetically slower and more distributive with substantially more pausing than that seen in the 1/16x lanes in FIG. 2. Collectively, FIGS. 1 and 2 indicate that limited dNTP pools contribute to the delayed proviral HIV-1 DNA synthesis previously observed in macrophages (Diamond et al. *J. Biol. Chem.* 279:51545-51553 (2004); and O'Brien et al., *J. Virol.* 68:1258-1263 (1994)). This is consistent with the observation that HIV-1 proviral DNA synthesis is accelerated by elevating cellular dNTP pools in non-dividing cells, but not in dividing cells, which already have dNTP levels well above the $K_d$ and $K_m$ of HIV-1 RT (Jamburuthugoda et al. *J. Biol. Chem.* 281:13388-13395 (2006); and Piccirilli et al., *Nature* 361:85-88 (1993)).

Example 3

Figures 3A, 3B, 3C:
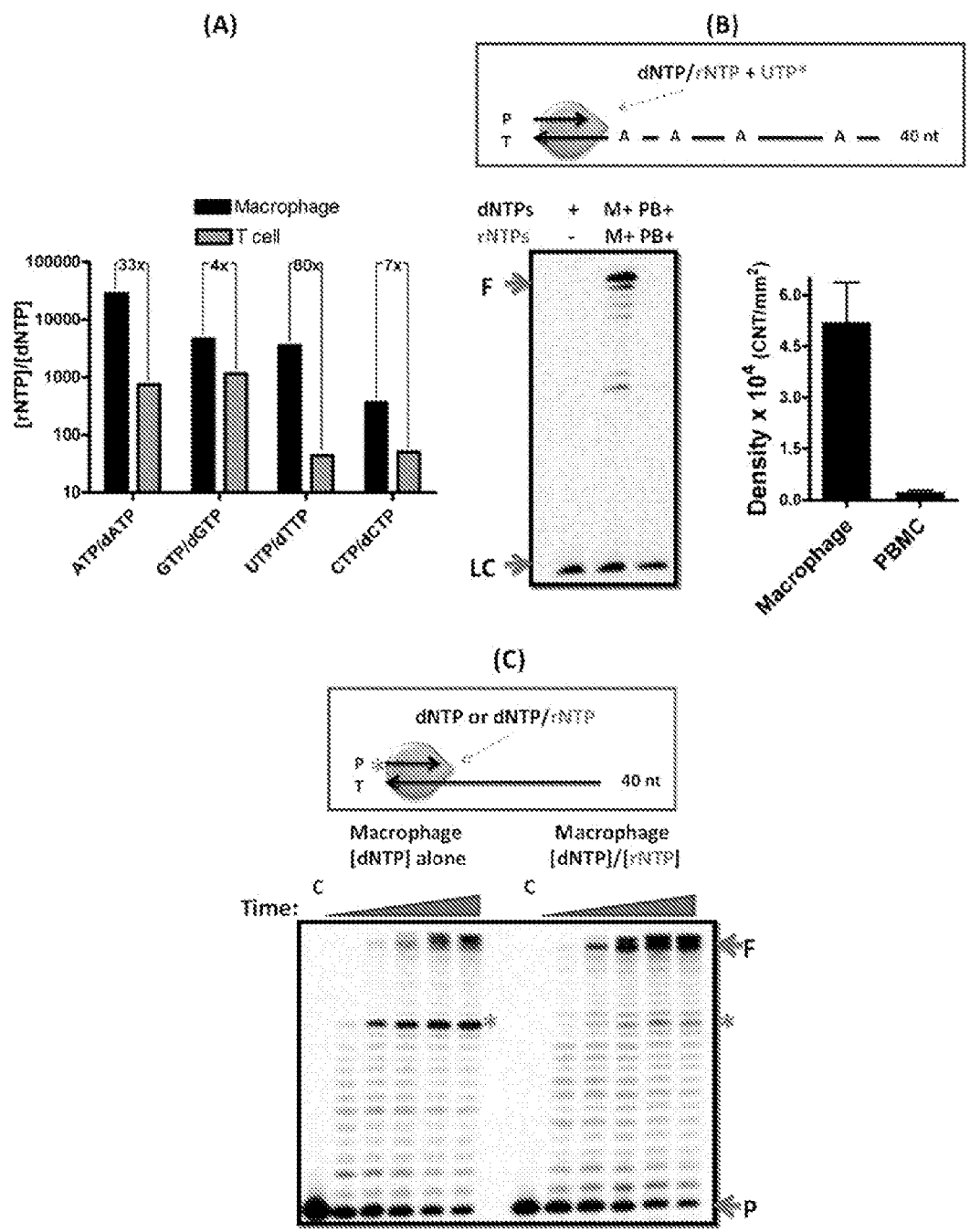
FIGS. 3A-3E show HIV-1 RT mediated incorporation of rNTPs at intracellular concentrations found in primary human HIV-1 target cell types.

Retrovirus RT Incorporates rNTP from Cellular dNTP/rNTP Pools Found in Retrovirus Target Cell Types One key observation revealed by quantification of dNTP and rNTP concentrations in the two retrovirus target cell types, summarized in Table 1, is that rNTP and dNTP concentration disparities exist in nondividing cells, e.g., macrophages, and dividing cells, e.g., activated PBMCs. As illustrated in FIG. 3A, due to the relatively high rNTP concentrations and extremely low dNTP concentrations, non-dividing cells display 4-80 times greater disparity between rNTP and dNTP concentrations than those in dividing cells. Accordingly, the ability of retrovirus RT to opportunistically incorporate rNTPs in the macrophage environment, particularly when DNA synthesis kinetics are largely compromised due to the limited dNTP pools, was assessed.

Figure 3D:
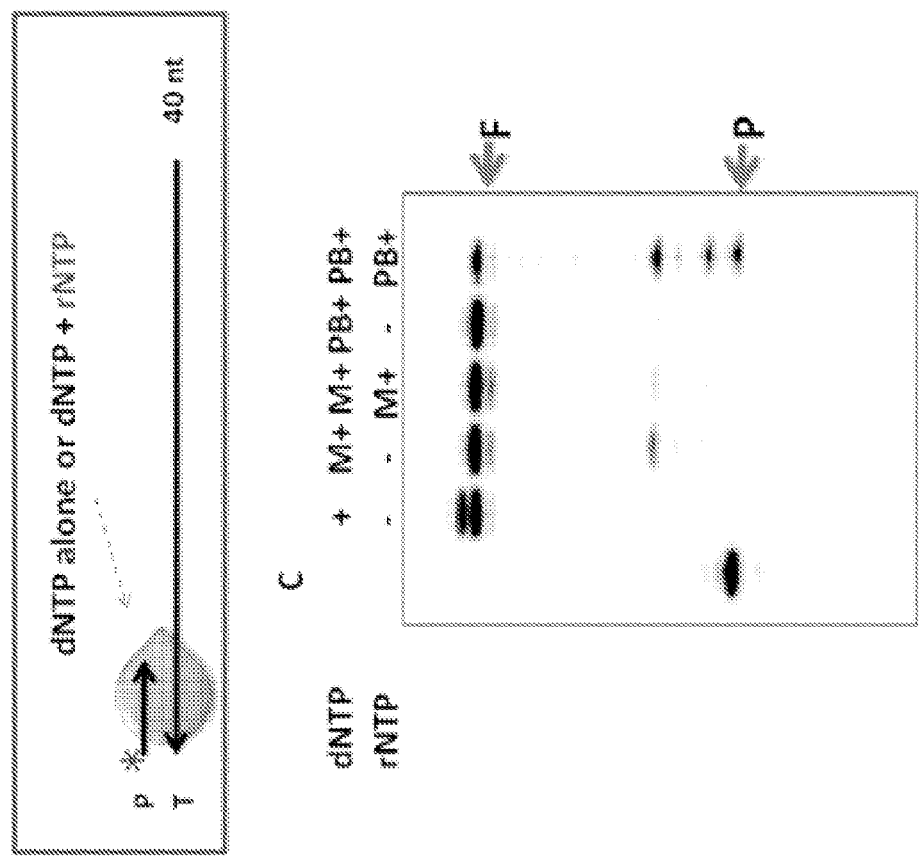

Primer extension/DNA synthesis reactions of HIV-1 RT (green circle in FIGS. 3B and 3C) with a non-radioactive 23-mer primer annealed to a 40-mer RNA template in the presence of dNTP and rNTP concentrations found in non-dividing and dividing cells (Table 1 and FIG. 3A). To visualize the incorporation of rNTPs during DNA synthesis, low levels of α-$^{32}$P-UTP (1/690 of non-radioactive UTP concentrations) were included in the simulated nucleotide pools. As shown in FIG. 3B (left panel), the polymerase reaction of HIV-1 RT with dNTPs alone did not generate any visible bands in the absence of rNTP, which was expected. However, fully extended, radiolabeled products (F) were detected in reactions performed using dNTP/rNTP pools found in non-dividing cells (FIG. 3B). In contrast, no radiolabeled extension products were detected in reactions performed using dNTP/rNTP pools found in dividing cells (FIG. 3B). Control experiments with a 5' end $^{32}$P-labeled primer confirmed the efficient extension of the primer and the production of full-length products in both the dividing and non-dividing cell environments (FIG. 3D). Thus, the absence of a radiolabeled extension product under the conditions found in dividing cells (FIG. 3B) reflects a lack of rNTP incorporation, and not a failure to complete DNA synthesis. Quantification of the radioactively labeled extended products in FIG. 3B (right panel) revealed that rNTP incorporation in the non-dividing cell environment was 22 times more efficient than in the dividing cell environment.

Figure 3E:
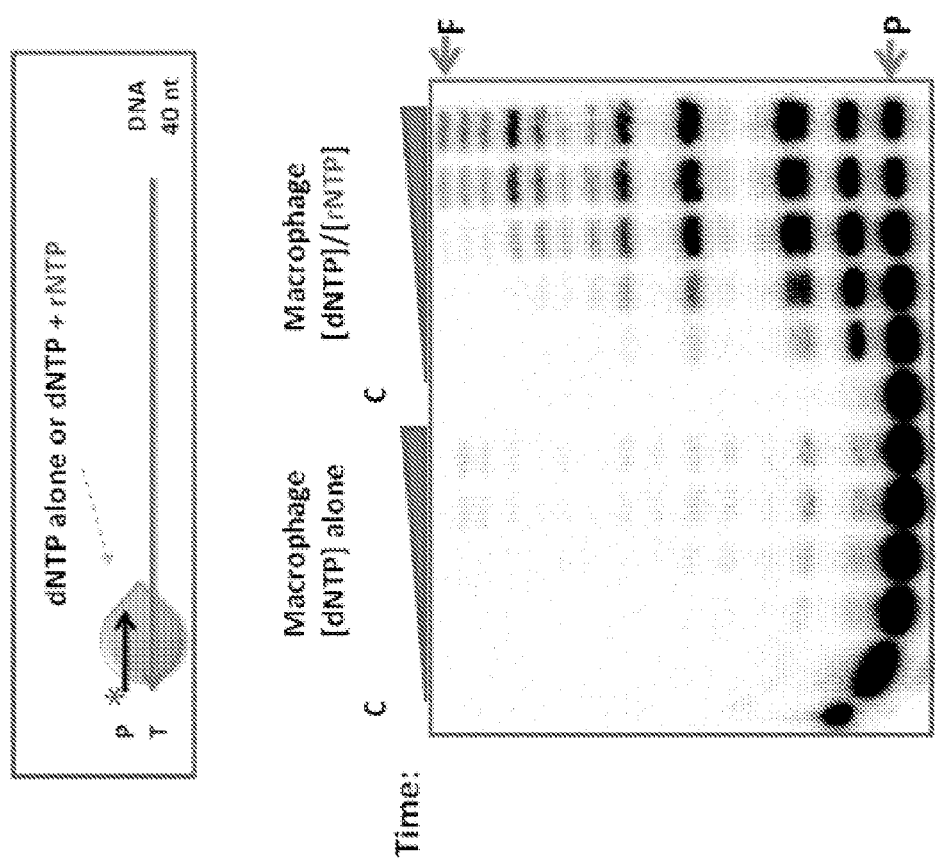

Next, the impact of non-dividing cell nucleotide pools on the entire ensemble of RT-mediated DNA synthesis was evaluated. A time course primer extension reaction using a 5' end $^{32}$P-labeled 17mer annealed to an RNA 40mer was employed. Unlike in FIG. 3B, which shows only extension products that have incorporated a radiolabeled rNTP, this analysis revealed all extended primer products since the primer itself is labeled. FIG. 3C shows the efficiency of DNA synthesis by HIV-1 RT in the non-dividing cell environment that contained either dNTPs alone or dNTPs plus rNTPs. The results revealed that RT-mediated DNA synthesis was enhanced by the presence of rNTPs in the non-dividing cell environment, as reflected by an increase in fully extended synthesis products (F) and a reduction in paused products (*). These results indicate that rNTPs serve as substrates for retrovirus RT in a non-dividing cell environment. Importantly, a similar kinetic enhancement by rNTPs was also observed during DNA synthesis of retrovirus RT with DNA template in the nucleotide pools found in non-dividing cells (FIG. 3E), indicating that retrovirus RT can incorporate rNTPs during both (+) and (−) strand proviral DNA synthesis in the non-dividing cell nucleotide environment. In addition, as predicted by the lack of rNTP incorporation (FIG. 3B), no kinetic enhancement by rNTPs was observed in the nucleotide pools found in dividing cells (data not shown).

Example 4

Figures 4A, 4B, 4C:
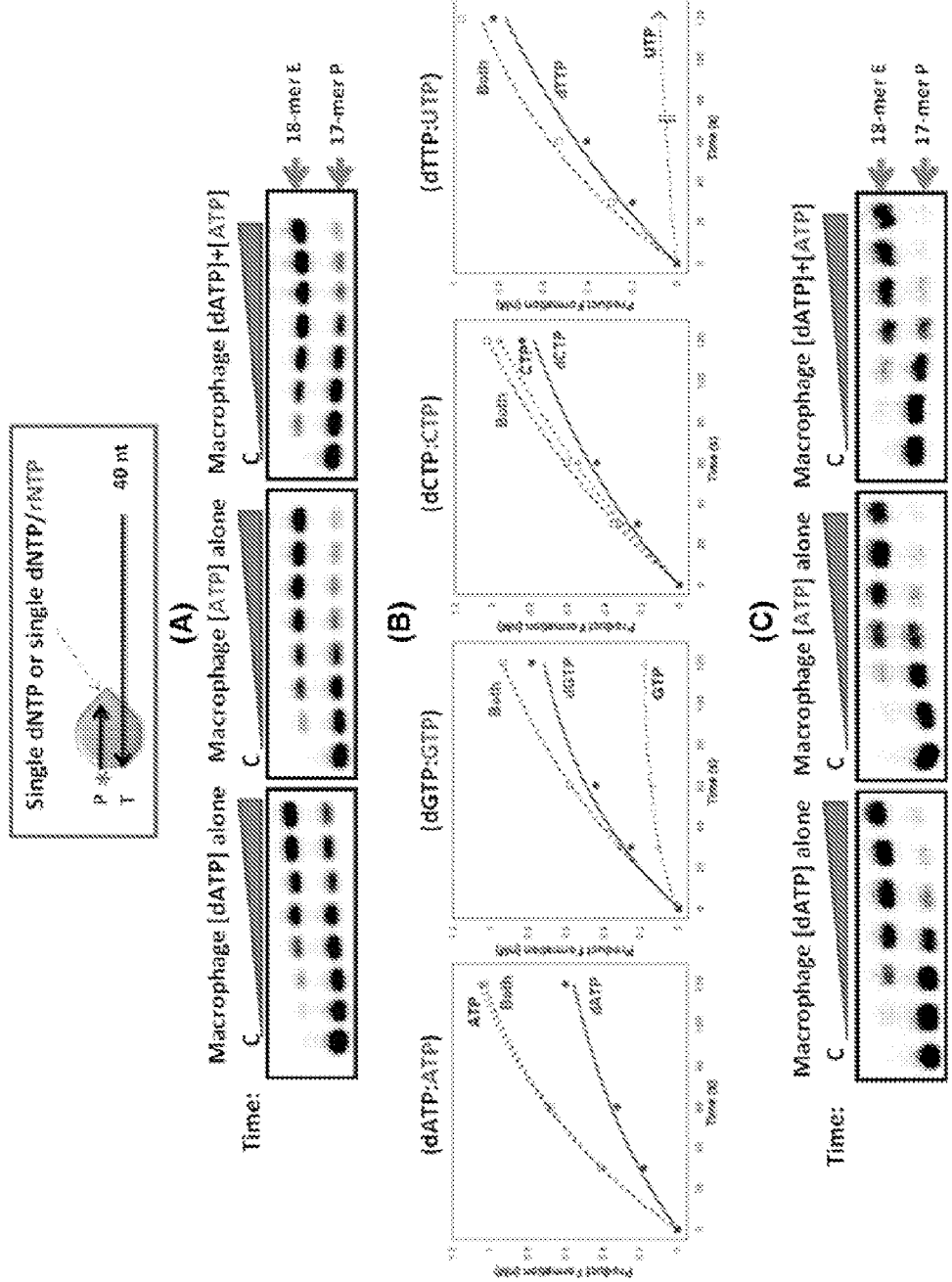
FIGS. 4A-4E compare the dNTP and rNTP incorporation rates of HIV-1 RT at nucleotide concentrations found in human macrophages. Incorporation kinetics of HIV-1 RT (green circle) for individual dNTPs and rNTPs at their concentrations found in macrophages (see Table 1) were compared by single nucleotide extension reactions.

Comparison of dNTP and rNTP Incorporation Rates of Retrovirus RT with the Nucleotide Pools Found in Non-Dividing Cells The incorporation kinetics for individual dNTPs and rNTPs by retrovirus RT at the concentrations found in non-dividing cells were assessed. For this, a primer extension reaction similar to that used in FIG. 3C was employed, except nucleotide specific primers and a single dNTP, rNTP, or both were used to estimate individual nucleotide incorporation rates. As shown in FIG. 4A, HIV-1 RT incorporates dATP and ATP at macrophage concentrations at similar levels. As summarized in FIG. 4B (blue dotted lines), HIV-1 efficiently incorporates ATP and CTP, but less efficiently GTP and UTP. Upon combining dNTPs and rNTPs in a reaction (FIGS. 4A and B, purple dotted lines), the total single nucleotide extension rate appeared to be elevated as compared to the rates of either dNTP (red line) or rNTP alone. When primer extension products were plotted by time, primer extension was accelerated in the presence of both dNTPs and rNTPs at their macrophage concentrations as compared to the reactions containing either dNTPs or rNTPs alone. The results of this single nucleotide assay are consistent with the data from the multiple nucleotide incorporation assay (FIG. 3C). These data indicate that rNTPs, which are normally the substrates of RNA polymerases, are not only incorporated into DNA by retrovirus RT, but also enhance the rate of DNA synthesis in a non-dividing cell environment.

Next, the RT of simian immunodeficiency virus (SIV$_{agm}$ Sab) (SIV RT), which is another lentivirus capable of infecting non-dividing cells, was evaluated for its ability to incorporates rNTPs as well as dNTPs under conditions present in non-dividing cells. As shown in FIG. 4C, SIV RT also utilizes ATP at the concentration found in non-dividing cells, and the addition of ATP to dATP resulted in more efficient DNA synthesis. These results demonstrate that effective utilization of rNTPs during DNA synthesis is a feature common among lentiviral RTs that replicate in non-dividing cells.

Example 5

Steady State Kinetic Analysis of Retrovirus RT rNTP Incorporation

Figures 4D, 4E:
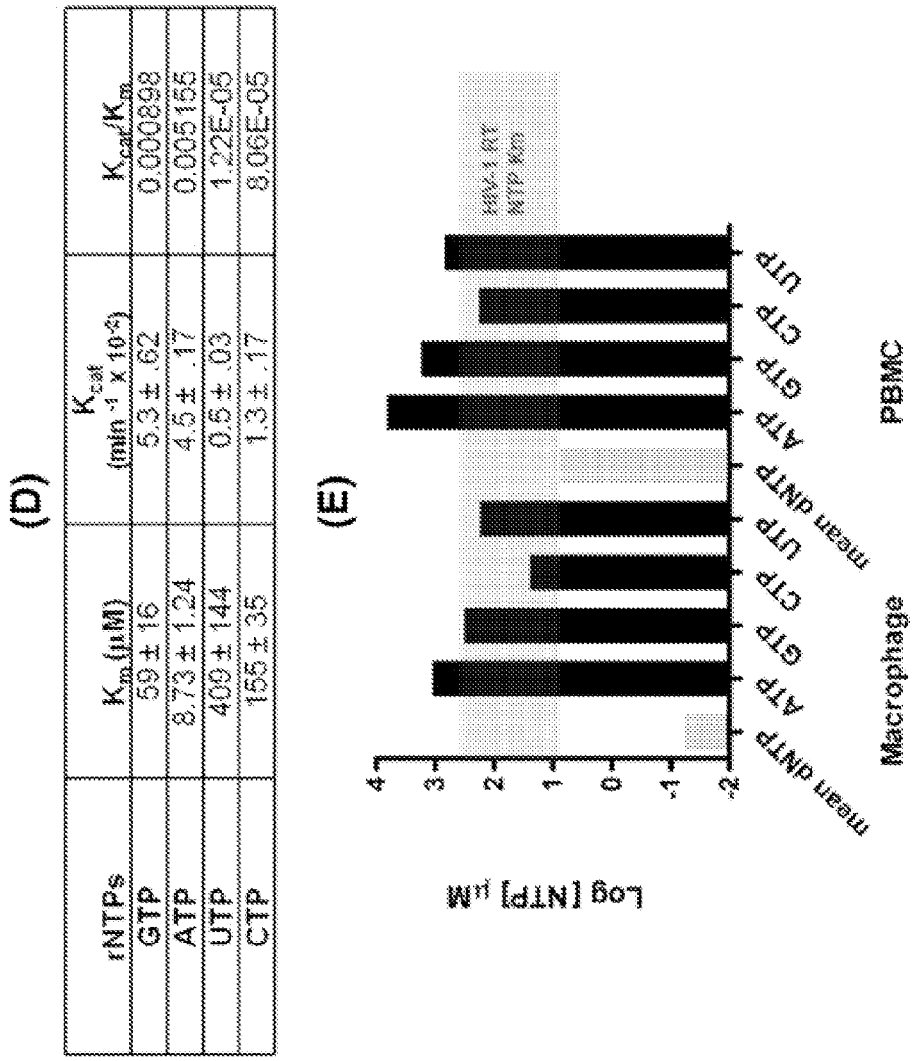

The enzymatic efficiency of rNTP incorporation by retrovirus RT was evaluated. $K_m$ values of HIV-1 RT for rNTPs using a single nucleotide extension assay were determined and compared to the cellular rNTP concentrations found in non-dividing and dividing cells. As summarized in FIGS. 4D and E, the $K_m$ values for ATP and GTP were well within the range of cellular ATP and GTP concentrations found in non-dividing cells, while the $K_m$ values of UTP and CTP were higher than their concentrations in non-dividing cells. The data in FIGS. 4D and E also indicate that HIV-1 RT is capable of utilizing rNTPs when present at the concentrations found in activated T cells. However, rNTP incorporation is likely prevented in the activated T cell environment due to the high levels of dNTPs, which compete much more effectively for binding to RT and are preferred substrates (see FIGS. 3B and 3D).

Example 6

Effect of rNMP at the 3' End of the Primer on Retrovirus RT Activity

Figure 5:
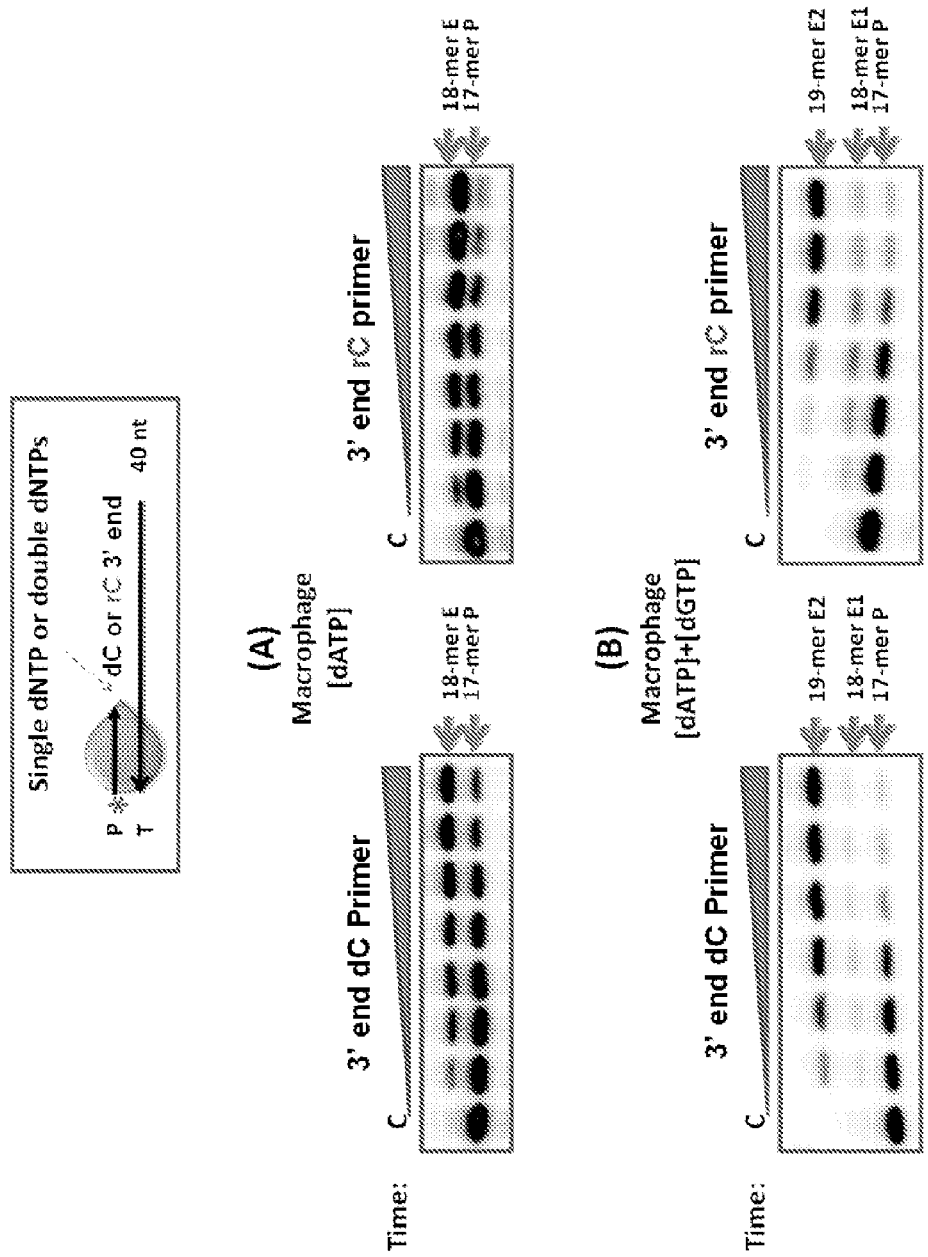
FIGS. 5A and 5B show the extension of DNA primers containing 3' end dCMP and rCMP by HIV-1 RT in macrophage dNTP concentrations. Included is a diagram of the template (T) and primers (P) used in these experiments: two 5' end $^{32}$P labeled DNA primers containing dCMP or CMP at their 3' ends were individually annealed to the RNA 40mer template.

Retrovirus RT was then evaluated for its ability to incorporate rNMP at the 3' end of a primer. Specifically, HIV-1 RT incorporation of a single dNTP into DNA primers containing either dCMP or rCMP at the 3' ends was measured. These two types of primers were 5' end $^{32}$P-labeled and annealed to a 40-mer RNA template (FIG. 5). These primers were extended by HIV-1 RT (20 nM) in the presence of the TTP concentration found in macrophages (40 nM). As shown in FIG. 5A, HIV-1 RT displayed an equal extension capability with both the 3' end rCMP and dCMP primers at the macrophage TTP concentration. Next, the same experiments were conducted except with both dATP and dGTP which are the first and second nucleotides to be incorporated, respectively. As shown in FIG. 5B, HIV-1 RT was also equally capable of incorporating the second nucleotide (dGTP) from both 3' end dCMP and rCMP primers. These results, i.e., efficient extension from 3' end rNMP, are consistent with the ability of retrovirus RT to initiates both (−) and (+) proviral DNA synthesis using RNA primers (e.g., tRNALys3 and polypurine tract RNA primer) containing 3' end rNMPs during viral replication.

Example 7

Inhibition of Retrovirus Proviral DNA Synthesis in Non-Dividing Cells by 3'-Deoxyadenosine As retrovirus RT can incorporate rNTPs in nucleotide pools found in non-dividing cells, rNTP analogs lacking 3'-OH, termed ribonucleoside chain terminators (rNCTs), were assessed for their ability to be incorporated during retrovirus replication and inhibit viral reverse transcription in non-dividing cells. Specifically, the effects of ribonucleoside chain terminator, 3'-deoxyadenosine (rACT), were evaluated.

First, the cytotoxicity of rACT in human primary CD4$^+$ T cells, human primary macrophages, human microglial CHME5, and human premonocytic U937 cell lines was assessed. Cells were incubated with different concentrations of rACT (up to 1 mM) for 2 days, and cell survival was determined. As shown in FIG. 6A, no significant cytotoxicity of rACT was observed in primary human cells or transformed cell lines at concentrations up to 1 mM. Next, rACT was evaluated for its ability to inhibit HIV-1 replication in non-dividing cells. The transduction efficiency of an HIV-1 vector in primary human macrophages in the presence and absence of rACT was measured. Human macrophages, which were prepared from multiple donors, were pre-incubated with various concentrations of rACT, and then transduced with an HIV vector (D3-GFP), which expressed all HIV-1 proteins except Env and Nef (replaced with eGFP). Virus infectivity was determined by FACS analysis for GFP expression at 7 days post infection. As shown in FIGS. 6B and 6C, treatment with rACT (0.1 and 1 mM) reduced the percent of macrophages expressing GFP as compared to no treatment. To confirm that the reduction of HIV-1 vector infectivity by rACT was not due to inhibition of cellular RNA polymerase-mediated transcription of the GFP gene or some other off-target effect, the copy number of HIV-1 2-LTR DNA circles was measured. HIV-1 2-LTR DNA circles are formed in the nucleus after the completion of reverse transcription and are commonly used to monitor HIV-1 proviral DNA synthesis kinetics (see Butler et al., *Nat. Med.* 7:631-634 (2001)). As shown in FIG. 6D, rACT (0.1 and 1 mM) substantially reduced the 2-LTR circle copy number in macrophages. Finally, the effect of rACT on HIV-1 infection in activated CD4+ T cells was examined. As shown in FIG. 6E, rACT had less of an inhibitory effect in activated T cells at both rACT concentrations as compared to macrophages (FIG. 6C). These results are consistent with the above findings indicating that ribonucleoside analogs are preferentially incorporated by retrovirus RT in cells where the disparity between dNTP and NTP is vastly larger (e.g., non-dividing cells such as macrophages) (FIG. 3A).

Figure 6:
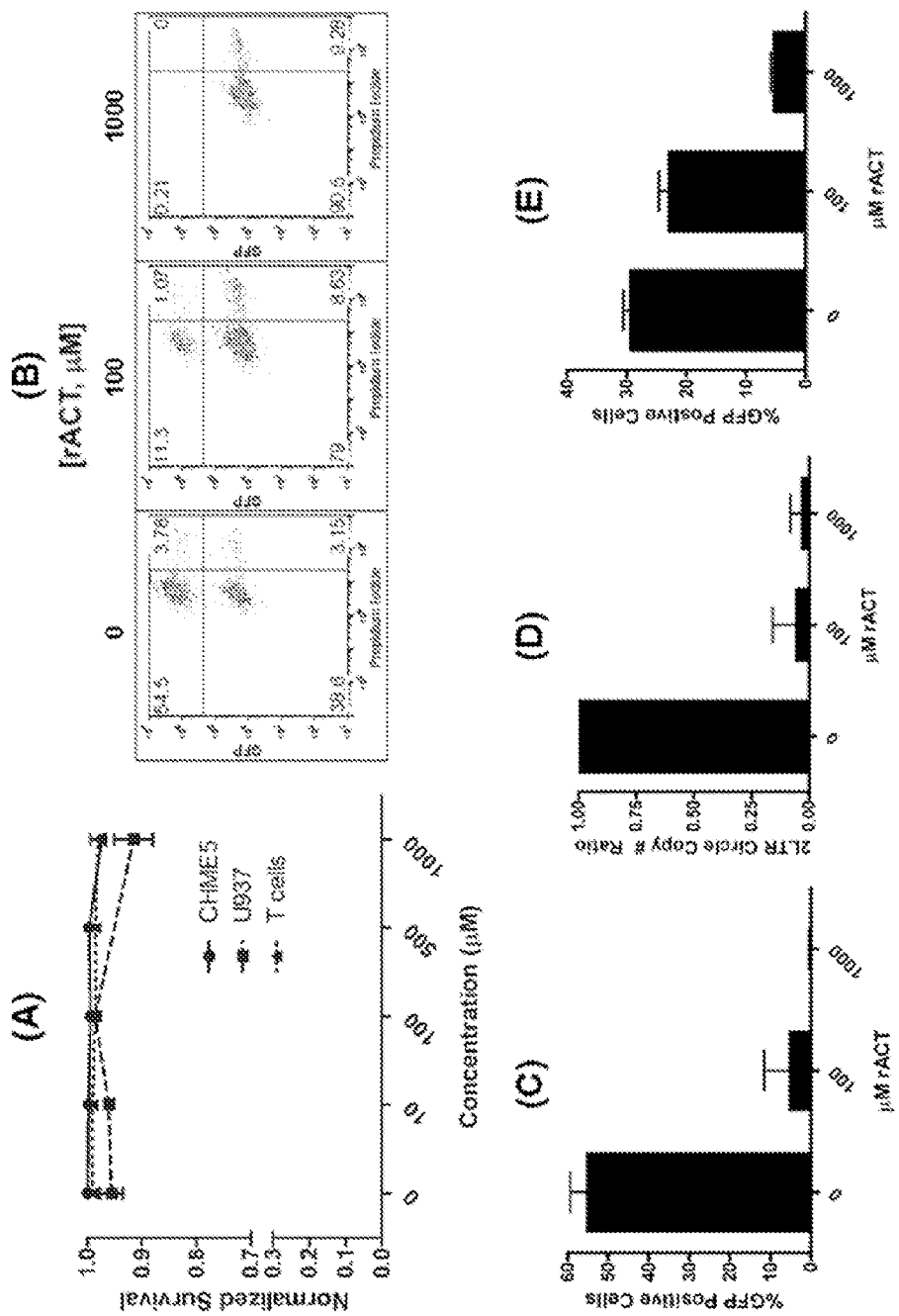
FIGS. 6A-6E show inhibition of HIV-1 reverse transcription by 3' deoxyadenosine chain terminator (rACT) in human primary macrophages and its cytotoxicity.

The data presented in FIG. 6 demonstrate that rACT effectively inhibits retrovirus reverse transcription in cells where there is a large disparity between dNTP and NTP levels (e.g., macrophages).

Example 8

LC-MS/MS-Based Quantitation of Cellular dUTP in Primary Retrovirus Target Cell Types Cellular dUTP concentrations in human primary cells have been previously reported. However, the reported dUTP concentrations significantly vary, and this could be due to technical difficulties in reliably differentiating dUTP from other chemically very close nucleotides such as UTP and TTP. Therefore, quantitative LC-MS/MS technology was employed to determine the dUTP and TTP concentrations of human primary macrophages and activated PBMCs isolated from multiple donors. The results are shown below in Table 2.

TABLE 2

Intracellular dUTP Concentrations of Primary Human Monocyte Derived Macrophages and Activated PBMCs as determined by LC-MS/MS.

|  | TTP | dUTP |
| --- | --- | --- |
|  | Concentration μM | |
| Activated PBMC | 16.0 ± 5.25 | 11.99 ± 1.67 |
| Macrophage | 0.05 ± 0.04 | 2.88 ± 1.34 |

TABLE 2-continued

Intracellular dUTP Concentrations of Primary Human Monocyte Derived Macrophages and Activated PBMCs as determined by LC-MS/MS.

|  | TTP | dUTP |
| --- | --- | --- |
|  | pmol/10$^6$ cells | |
| Activated PBMC | 4.85 ± 1.56 | 3.84 ± 0.53 |
| Macrophage | 0.13 ± 0.1 | 7.66 ± 3.57 |

Figure 7:
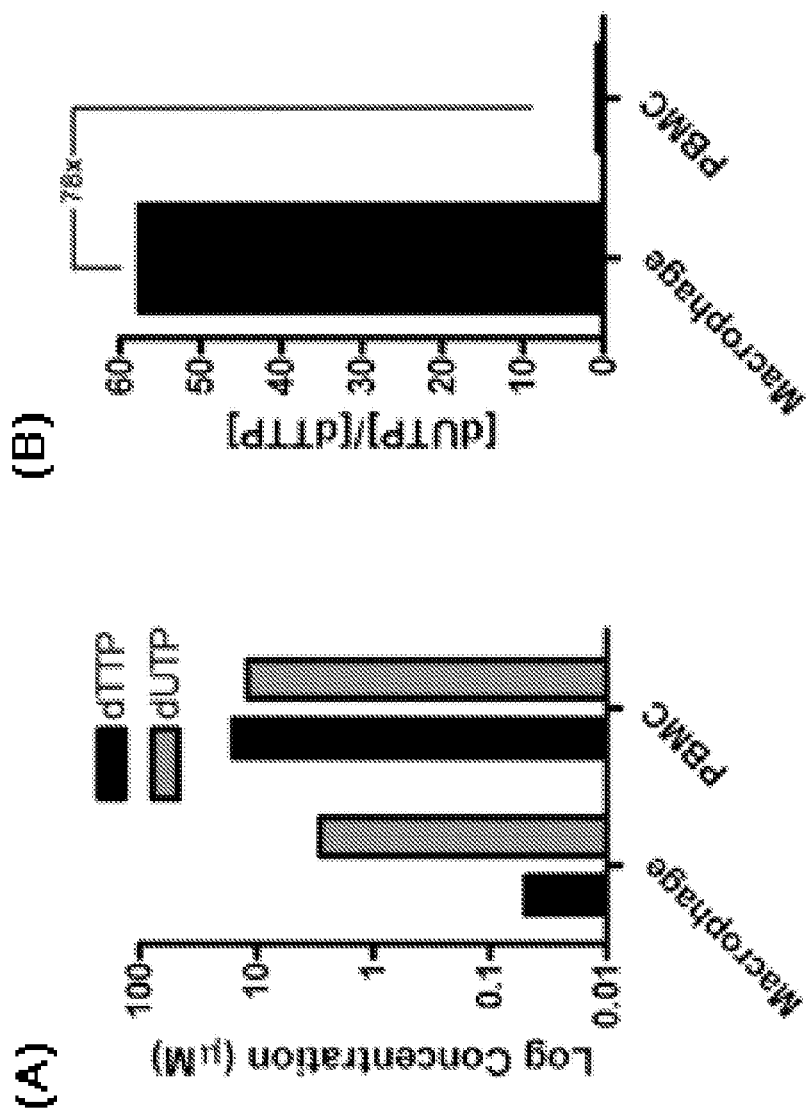
FIGS. 7A and 7B compare dUTP/dTTP concentrations of human primary macrophages and activated PBMCs.

These results show that human macrophages harbor much lower TTP concentration than activated PBMCs. However, unlike canonical dNTPs, macrophages still maintain a high dUTP concentration, such that the observed [dUTP]/[dTTP] ratio was 58. When this ratio is compared to actively dividing PBMCs, there is 78 fold difference (FIG. 7).

Example 9

Retrovirus RT Incorporates dUTP in Cellular dNTP/rNTP Pools Found in Non-Dividing Cells Retrovirus RT was assessed for its ability to incorporated dTTP and dUTP at physiologically relevant concentrations. First, $K_m$ of HIV-1 RT, SIV RT, MuLV RT, and FIV RT for both dTTP and dUTP was measured. The results are shown below in Table 3.

TABLE 3

Steady State Kinetic Parameters of HIV-1, MuLV, FIV, and Sab-1 Reverse Transcriptases for dTTP/dUTP.

|  |  | $K_m$(uM) | $K_{cat}$ | $K_{cat}/K_m$ | Selectivity (dTTP/dUTP) |
| --- | --- | --- | --- | --- | --- |
| HIV | dTTP | .0218 ± .0028 | .0096 ± .0028 | .4404 | 1.298 |
|  | dUTP | .0277 ± .0070 | .0094 ± .0031 | .3394 | — |
| SIV | dTTP | .0184 ± .0043 | .0010 ± .0002 | .0543 | 0.839 |
|  | dUTP | .0170 ± .0035 | .0011 ± .0001 | .0647 | — |
| FIV | dTTP | .0586 ± .0066 | .0390 ± .0006 | .6655 | 3.754 |
|  | dUTP | .1799 ± .0045 | .0319 ± .0013 | .1773 | — |
| MuLV | dTTP | .0504 ± .0220 | .0008 ± .0001 | .0159 | 4.969 |
|  | dUTP | .2532 ± .0521 | .0008 ± .0001 | .0032 |  |

From these results, it is clear that retrovirus RTs such as SIV RT and HIV-1 RT are minimally selective for dUTP. To confirm that selectivity is not pronounced during the binding or isomerization steps of polymerization, pre-steady state quench flow titrations for dTTP and dUTP were performed with HIV-1 RT. The results are shown below in Table 4.

TABLE 4

Pre-Steady State Kinetic Parameters of HIV-1 RT for dTTP/dUTP.

| | $K_d$ (μM) | $K_{pol}$ (S$^{-1}$) | $k_{pol}/k_d$ (μM$^{-1}$ S$^{-1}$) | Selectivity |
| --- | --- | --- | --- | --- |
| dTTP | 3.4 ± 0.62 | 85.72 ± 7.3 | 25 | 1.0 |
| dUTP | 5.1 ± 1.93 | 194.39 ± 30.0 | 38 | 1.52 |

These results further confirm that retrovirus RTs such as HIV-1 RT are minimally selective for dTTP. As such, dUTP incorporation is determined by the cellular dUTP/dTTP ratio (FIGS. 7A and 7B).

Figures 8A, 8B:
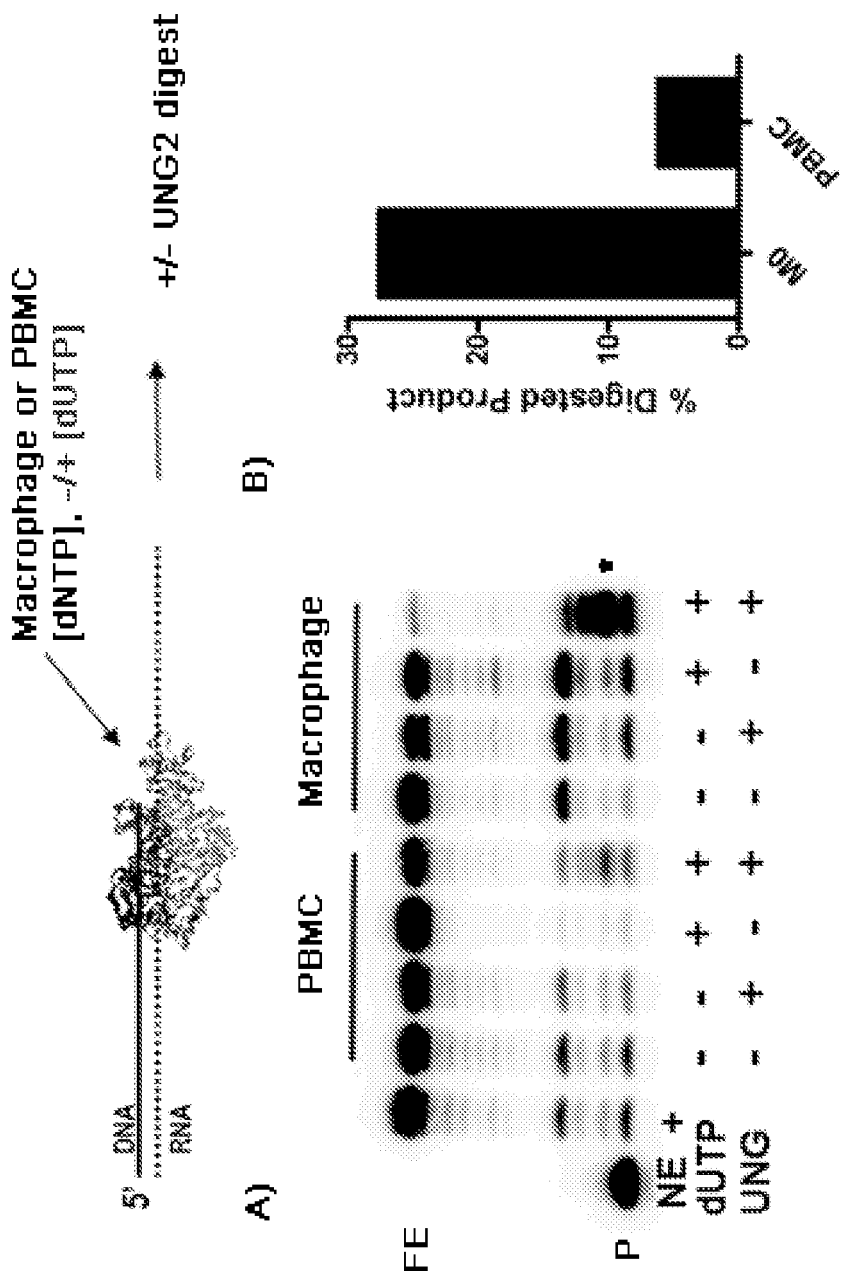
FIGS. 8A-8D show that dUTP is readily incorporated within substrate pools found in primary human macrophages.
Figures 8C, 8D:
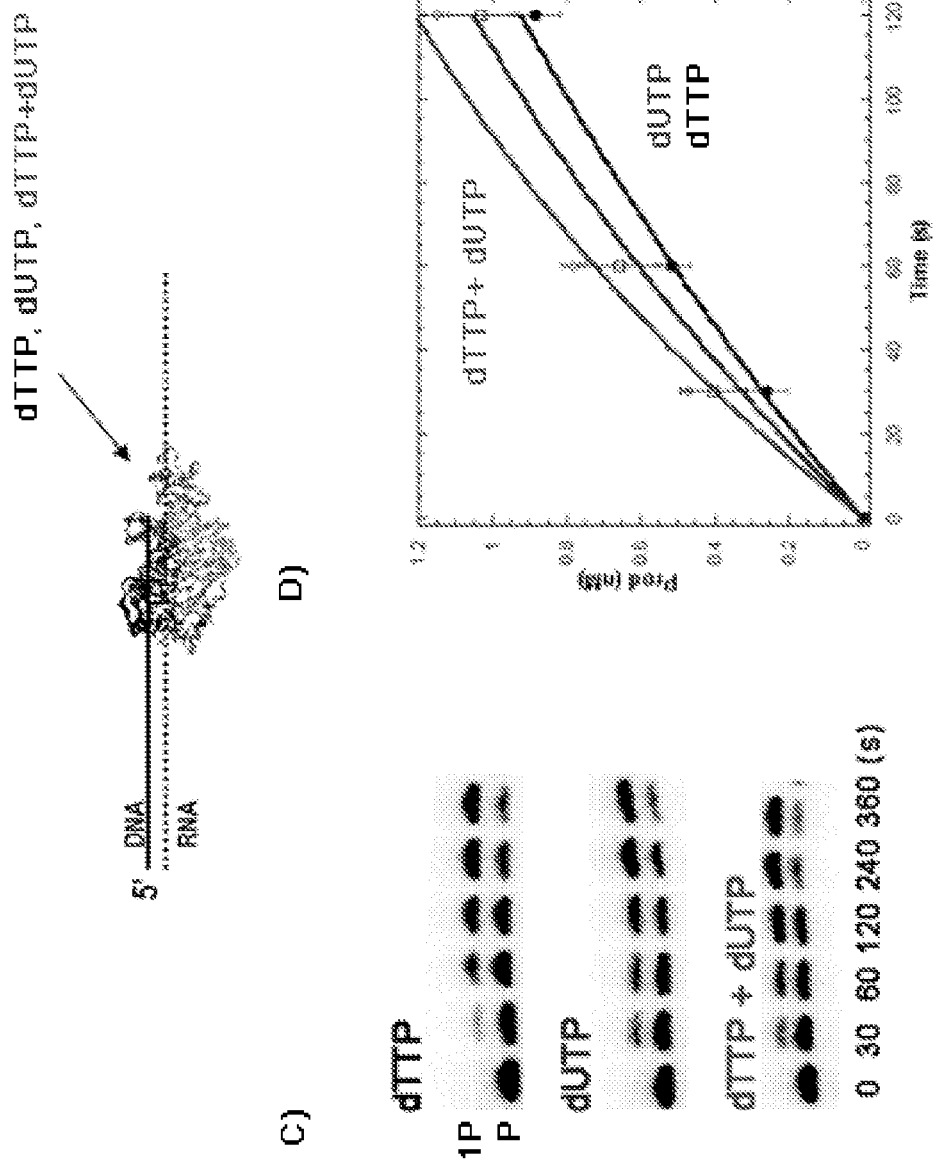

HIV-1 RT mediated DNA synthesis in nucleotide pools found in dividing and non-dividing cells was further assessed using a primer extension assay followed by *E. coli* UNG2 digestion to quantify the amount of dUTP incorporated under these condition (FIG. 8). The presence of a high molecular weight band at the first dTTP/dUTP incorporation site was used to monitor the fraction of DNAs that contained a dUTP following UNG digestion (see * in FIG. 8). The results indicate that there was a small amount of dUTP incorporation under dividing cell conditions (~6%). However, in reactions containing dUTP and dNTP levels found in non-dividing cells, dUTP incorporation accounted for almost ⅓ of all synthesized DNA, indicating that the amount of dUTP incorporation is approximately 5 fold higher in the non-dividing cell environment as compared to the dividing cell environment (FIG. 8B). These results were confirmed using a single nucleotide extension assay (FIGS. 8C and 8D). The single nucleotide extension assays were performed to compare the rate of incorporation dTTP, dUTP, or both nucleotides at concentrations found in non-dividing cells. The results affirmed that retrovirus RTs such as HIV-1 RT incorporate dUTP in non-dividing cell conditions.

Example 10

RTs from Lentiviruses not Having a dUTPase Readily Incorporate dUTP

Lentiviruses are unique in that they are able to infect and replicate in non-dividing cells, e.g., macrophages. As such, these viruses usually encode or hijack the cell's machinery to either prevent incorporation of dUTP or repair incorporated dUMP. Lentiviruses such as Feline Immunodeficiency Virus (FIV), Equine Infectious Anemia Virus (EAIV), Caprine Arthritis Encepalitis Virus (CAEV), and Visma Maedi Virus encode a dUTPase to hydrolyze dUTP prior to or during reverse transcription. However, the flux of small molecules (nucleotides) through the capsid may saturate the dUTPase with substrate, and the dUTP/dTTP ratio may be reduced to a level where reverse transcription may yield viable provirus. Thus, RTs from lentiviruses having a dUTPase may also have evolved mechanisms to be selective for TTP. In contrast, HIV-1 and SIV bind and package cellular UNG, which may repair incorporated dUTP post reverse transcription. As such, RTs from lentiviruses not encoding a dUTPase have not had to evolve a mechanism to selectively bind and/or incorporate TTP.

Figures 9A, 9B:
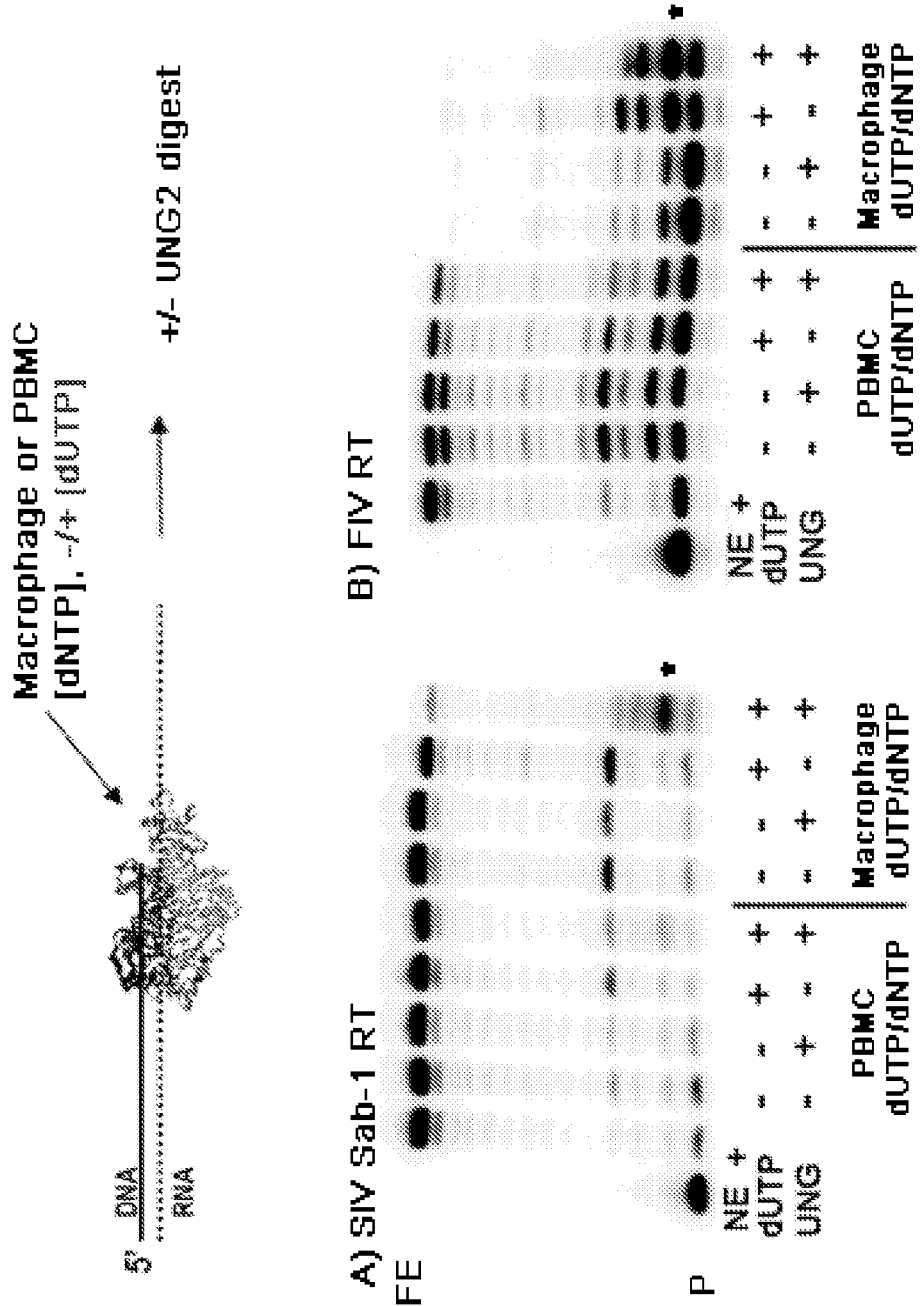
FIGS. 9A-9D compare the TTP selectivity of retroviral RTs. UNG-2 digestion assays were carried out with SIV$_{Sab1}$ RT, FIV RT, Foamy Virus RT, and MuLV RT.

The steady state kinetic data for HIV-1 RT, SIVagm Sab1 RT, and FIV RT confirm this idea. Of these RTs, FIV RT was the only RT found to be selective for TTP (Table 3). In addition, pre-steady state kinetic data of HIV-1 RT dUTP and TTP incorporation also confirmed that HIV-1 RT was not selective for TTP (Table 4). Furthermore, the results reported herein demonstrate that FIV RT TTP selectivity corresponds with reduced dUTP incorporation as measured in the UNG digestion assay (FIG. 9B). In contrast, HIV-1 RT (FIG. 8A) and SIV-1 RT (FIG. 9A) did not demonstrate such selectivity in the same assay.

Figures 9C, 9D:
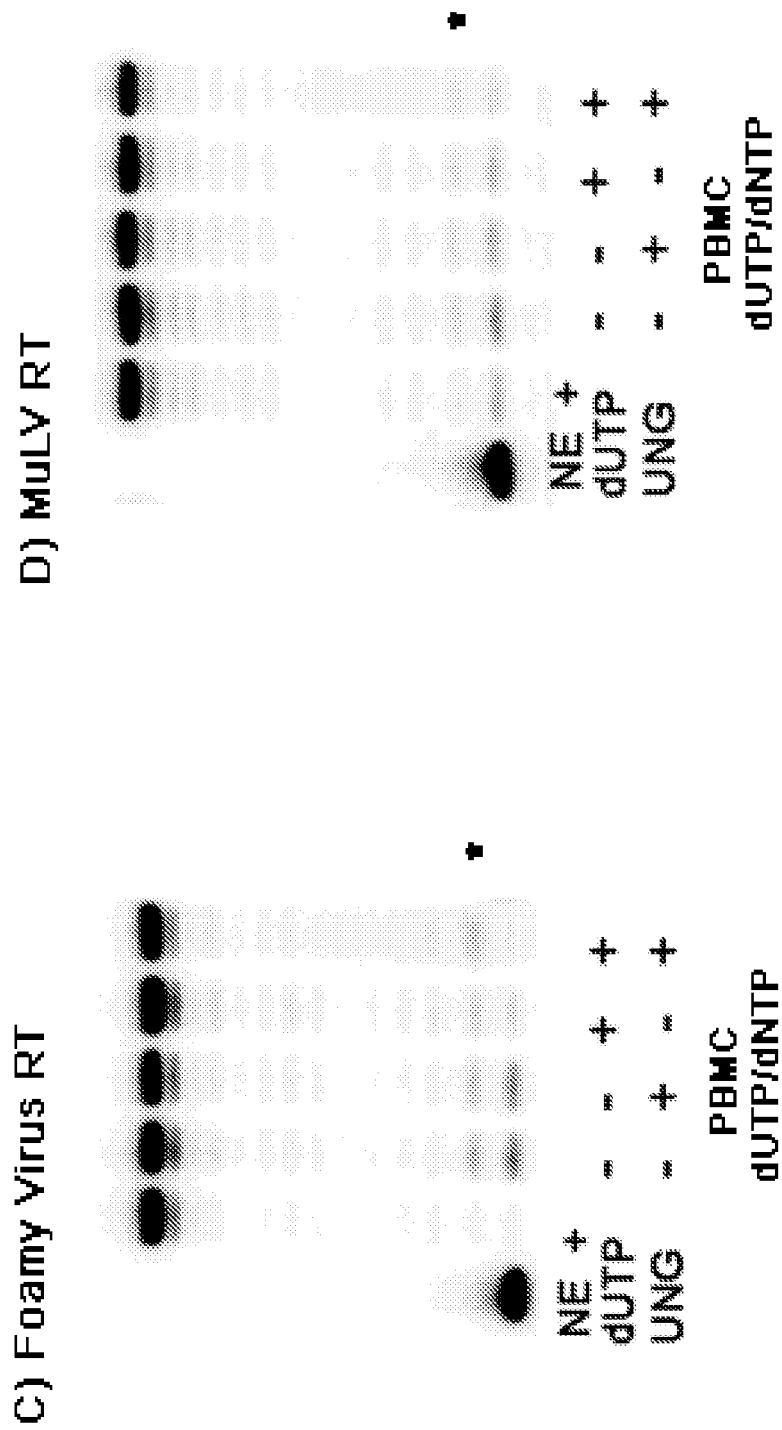

Finally, RT from two oncotretroviruses, which infect dividing cells, were assessed in the UNG2 digestion assay. Under PMBC conditions, MuLV RT and Simian Foamy Virus RT do not incorporate uracil (FIGS. 9C and 9D). These results are consistent with the steady state kinetic data for MuLV (Table 3), which shows that MuLV RT is selective for TTP.

Example 11 ddUTP is a Potent Inhibitor of Reverse Transcription in Non-Dividing Cells

Figure 10A:
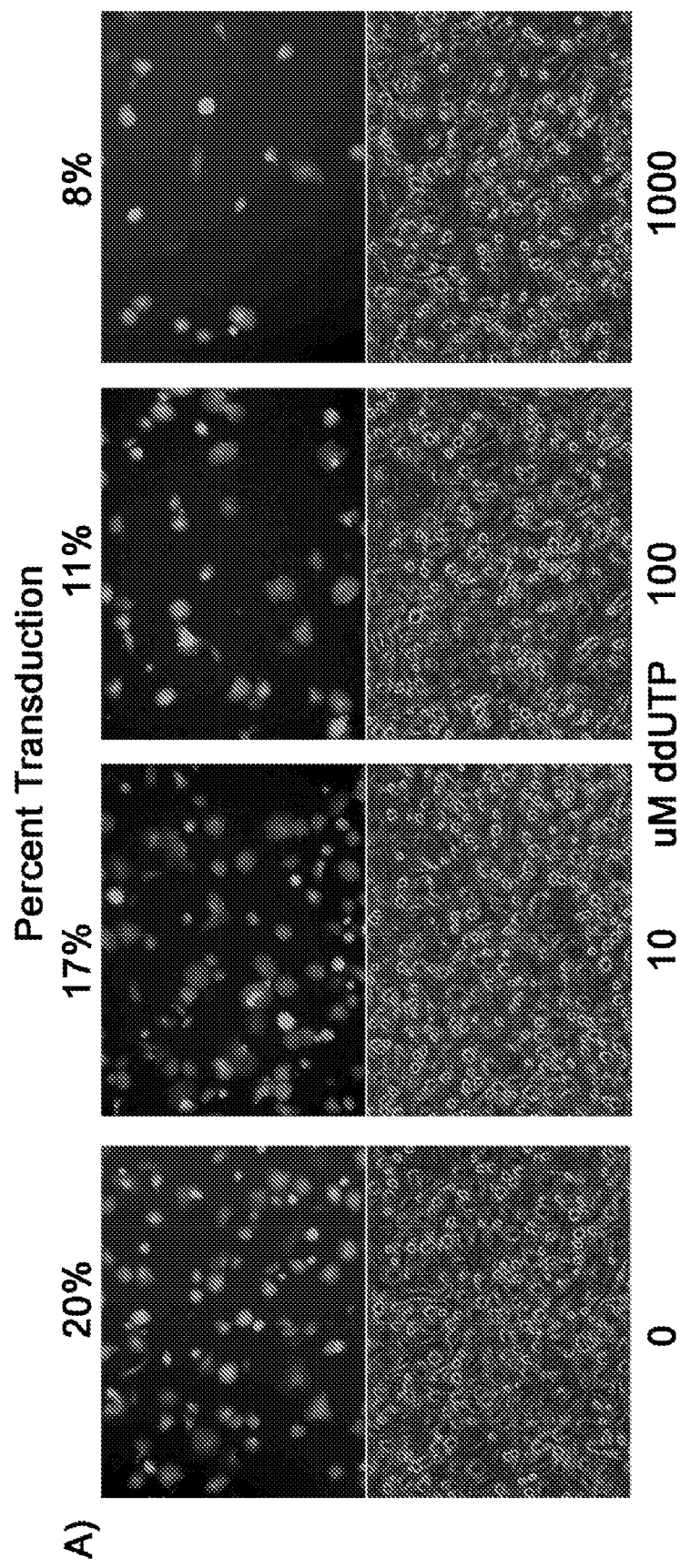
FIGS. 10A and 10B show that ddUTP inhibits HIV-1 replication in primary human macrophages. Primary human macrophages were pretreated with ddUTP and transduced with a single round VSV-G pseudotyped HIV-1 vector (D3HIV).
Figure 10B:
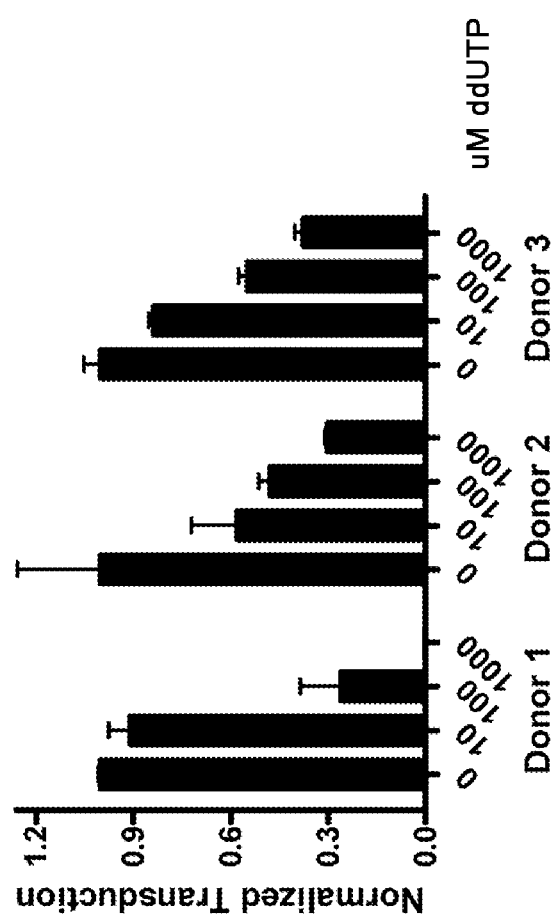
Figures 11A, 11B:
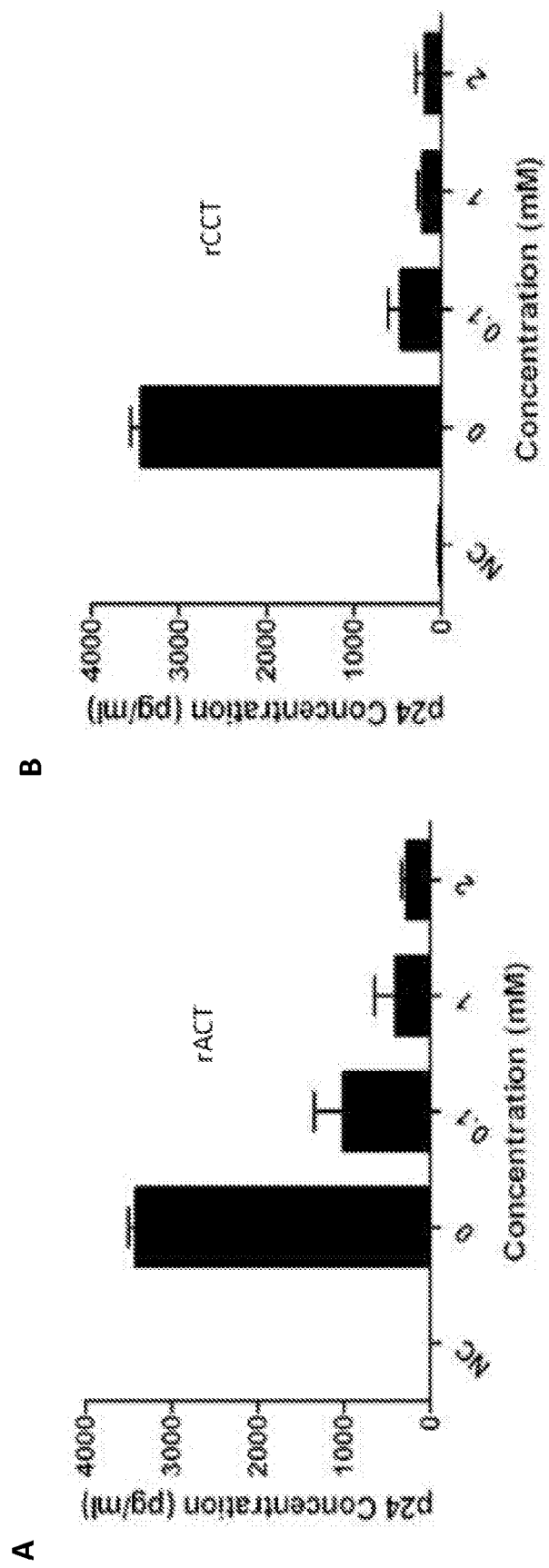
FIGS. 11A-11D show the antiretroviral effect of rACT, rCCT, rGCT, and rUCT in macrophages. Human primary macrophages were infected with M-tropic YU-1 HIV in the presence and absence of each rNCT (0, 0.1, 1 and 2 mM) for 7 days. Viral production was monitored by p24 ELISA.
Figures 11C, 11D:
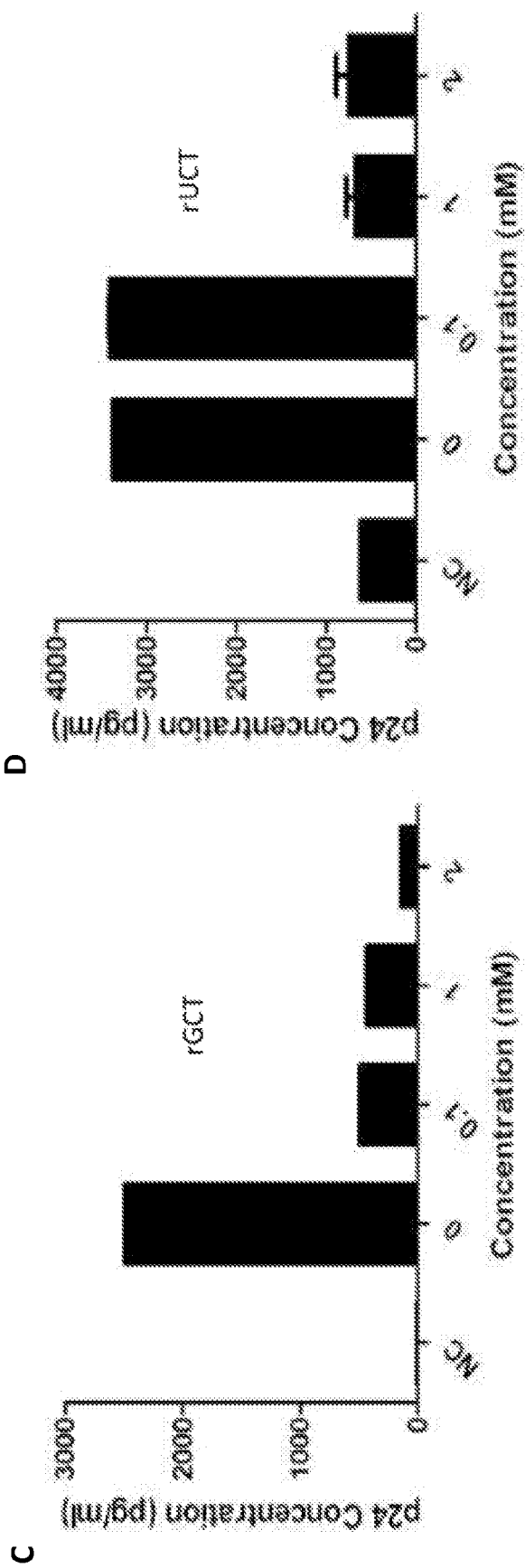

Dideoxy uracil triphosphate (ddUTP) was assessed for its ability to inhibit viral reverse transcription in non-dividing cells. Primary human macrophages and CD4$^+$ T-cells were isolated from human buffy coats and pretreated with ddUTP. The treated cells were then transduced with a single round of VSV-G pseudotyped HIV-1 vector D3-HIV in the presence of various concentrations of drug. When eGFP positive live macrophages were measured by flow cytometery, a dose dependent inhibition of transduction was observed in ddUTP treated cells (FIG. 10B), with little cell death as observed by brightfield microscopy (FIG. 10A) at the experimental endpoint or by propidium iodide staining. Little or no reduction in transduction efficiency was observed in CD4$^+$ T cells, where there are 320 fold higher levels of dTTP and 4 fold higher dUTP to dilute the ddUTP. To verify that these results were due to reduced levels of viral reverse transcription, the samples were analyzed by 2LTR QT-PCR assay. These QT-PCR assay results showed that 2LTR circles accumulated in the cells treated with higher concentrations of drug, indicating that ddUTP inhibits reverse transcription.

Example 12

Anti-Retroviral Effect of rNCTs in Dividing Cells

A continuous HIV-1 culture system in human primary macrophages was employed to validate the anti-retroviral effects of rNCT compounds in non-dividing cells. This assay used an infectious M-tropic YU-2 HIV-1 strain, which was cloned from HIV-1 infected microglia, i.e., a brain macrophage. Human primary macrophages infected with YU-2 (MOI of 0.05) were cultured for 12 days and viral production was monitored by p24 ELISA. As shown in FIGS. 11A-11D, significant reductions in viral production were observed at 100 µM rNCT, demonstrating that ribonucleoside chain terminators have anti-retrovirus effects in macrophages.

Figure 12:
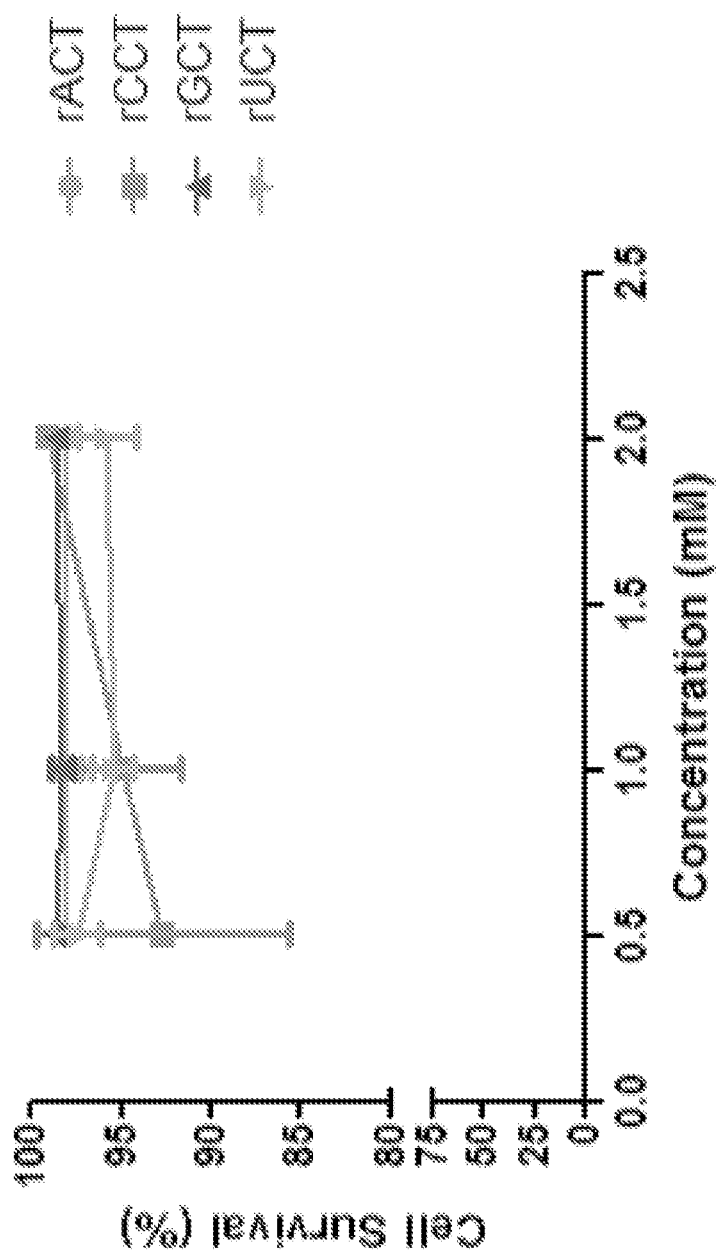
FIG. 12 shows that rNCTPs are not toxic to macrophages. Human primary macrophages were incubated in the presence or absence of rACT, rCCT, rGCT, or rUCT (0.5, 1 and 2 mM) for 7 days, and the percent of live cells (cell survival rate) were determined by propidium iodide-based FACS.

The continuous HIV-1 culture system in human primary macrophages was also employed to evaluate the toxicity of rNCTs in nondividing cells. Human primary macrophages were incubated in the presence or absence of each rNCT (0.5, 1 and 2 mM) for 7 days, and the percentage of live cells (cell survival rate) were determined by propidium iodide-based FACS. No significant cytotoxicity was observed for any of the rNCTs during macrophage culture (FIG. 12).

Retroviruses are unique in their ability to infect and replicate in terminally differentiated/non-dividing cells. Although terminally differentiated/non-dividing cells such as macrophages are post-mitotic, these cells still contain fully active transcriptional and cell signaling machinery for executing necessary biological functions. For example, rNTPs are substrates for transcription, cell signaling regulators, and energy carriers, and as described herein, terminally differentiated/non-dividing cells have high rNTP concentrations similar to those found in dividing cells. As reported herein, rNTPs are a preferred substrated utilized by retrovirus RTs in the cellular environment found in non-dividing cells, e.g., macrophages. Another significant finding was that 3' deoxy ribonucleoside chain terminators (rNCT) can inhibit retrovirus replication in non-dividing cells. These findings demonstrate that rNCTs are a new class of retroviral inhibitors specifically targeting the unique ability of retroviruses to infect terminally-differentiated/nondividing cells.

The results reported herein were obtained using the following methods and materials.

Preparation and Culture of Human Primary Macrophages and PBMCs

Human monocytes were isolated from buffy coats of HIV-1 negative, HBV/HCV negative donors with density gradient centrifugation coupled with enrichment for CD14$^+$ monocytes with Rosette Sep antibody cocktail (Stem Cell Technologies, Vancouver, British Columbia). Cells were seeded at a concentration of $1.0 \times 10^6$ cells/well (6-well plate) for 1 hour at 37° C., 5% CO2 to allow plastic adherence prior to repeated washes with 1×PBS. Monocytes were allowed to differentiate for 7 days in RPMI medium (Hyclone Logan, Utah) containing heat inactivated 20% fetal calf serum (FCS) (Atlanta Biologicals, Lawrenceville, Ga.), 1% Penicillin/Streptomycin (P/S) (Invitrogen, Carlsbad, Calif.), supplemented with 100 U/mL m-CSF (R&D Systems, Minneapolis, Minn.) at 37° C., 5% CO2. For all conditions, macrophages were stained with CD11b-APC (Miltenyi Biotec, Auburn, Calif.) and subjected to FACS to determine purity of >99%. Human PBMCs were also isolated from buffy coats derived from healthy donors. Activated PBMCs were maintained in RPMI media supplemented with heat inactivated 20% FCS, 1% P/S and 2% L-glutamine (Cellgro/Mediatech, Inc., Manassas, Va.); 6 µg/mL PHA (J-Oils Mills, Inc., Tokyo, Japan) was added to the cells 72 hours prior to experiments, in order to activate them.

Extraction of Intracellular Nucleotide Fraction and LC-MS/MS Analysis

For both macrophages and PBMCs, the isolated cells were washed twice with ice-cold 1×PBS to remove any residual medium. Cells were resuspended in 70% $CH_3OH$ overnight and extracts were centrifuged at 13,000 g for 10 min (Thermo Electron Corp., Marietta, Ohio). Supernatants were subsequently dried and resulting samples were reconstituted in HPLC mobile phase for LC-MS/MS analysis as previously described in Fromentin et al. *Anal. Chem.* 82:1982-1989 (2010). The rNTP level measurements were performed using a similar approach as described for dNTP. The stable isotopes, $[^{13}C^{15}N]ATP$, $[^{13}C^{15}N]GTP$, $[^{13}C^{15}N]CTP$, and $[^{13}C^{15}N]TTP$ were used for the measurement of ATP, GTP, CTP and UTP. The following m/z parent⇒ product MS/MS transitions, 523⇒ 146, 539⇒ 162, 496⇒ 119, and 495⇒ 81 were applied for the standard stable labeled isotopes and 508⇒ 136, 524⇒ 152, 484⇒ 112, and 485⇒ 81, for the corresponding sample nucleotides, respectively. For dUTP, the MS/MS transition 469=>81 was applied and $[^{13}C^{15}N]TTP$ was used for calibration.

Figure 2:
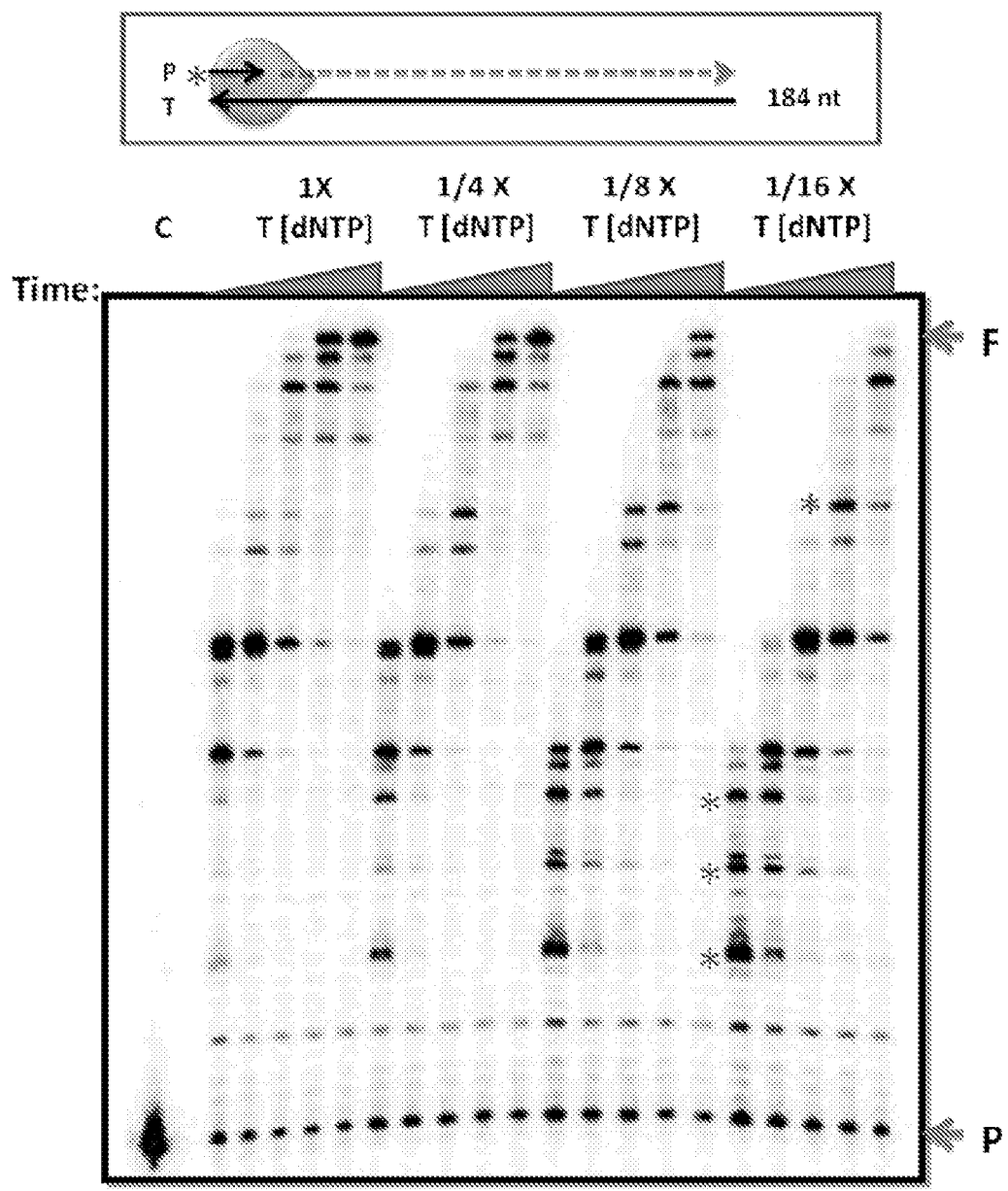
FIG. 2 includes a gel showing the DNA synthesis profile of HIV-1 RT in the range of the dNTP concentrations found in HIV-1 target cell types. A 5' end $^{32}$P 19mer DNA primer (P) annealed to 184-nt RNA template (T) encoding a portion of the HIV-1 NL4-3 gag gene was extended by HIV-1 RT (green circle, 40 nM) with the dNTP concentration found in human primary activated CD4+ T cells (1×: dATP, 23 nM; dGTP, 20 nM; dCTP, 30 nM; TTP, 32 nM); or its three serial dilutions (1/4×, 1/8× and 1/16×) for 0.5, 1, 2, 4, and 8 minutes. These reactions were analyzed by 10% polyacrylamide-urea denaturing gels. The pause sites are marked by "*"; F: fully extended product; P: unextended primer; and C: no RT control.

For the primer extension reactions of FIG. 2, a 5' end $^{32}P$ labeled 19-mer DNA primer annealed to the 184-nt region encoded in the HIV-1 NL4-3 gag gene was prepared as previously described in Balakrishnan et al. *J. Biol. Chem.* 276: 36482-36492 (2001); and Balakrishnan et al. *J. Virol.* 77:4710-4721 (2003).

Steady State Kinetics of HIV-1 RT with rNTPs

The single nucleotide incorporation reactions were conducted using 20 nM template/primers (40mer RNA template annealed to Primer A, Ext-T primer, Ext-G primer, or Ext-C primer) and 20 nM RT in 1× reaction buffer for 5 minutes at varying concentrations of NTP. Reactions were performed in triplicate.

Primer Extension with 3' End rNMP Primer

5' end $^{32}P$-labeled 23-mer Ext-T primer with either 3' end dCMP or rCMP was annealed to the 40-mer RNA template. 10 nM T/P was extended by 40 nM HIV-1 RT at the dNTP concentration found in macrophages under the 1× reaction buffer condition for varying lengths of time.

Visualization, Quantification, and Kinetic Analysis of the Primer Extension Reactions All primer extension reactions were analyzed with urea denaturing 10-16% PAGE gels and scanned with a phosphoimager (Biorad, Hercules, Calif.) and quantified with the Biorad Quantity One software. Nonlinear regression analysis was done with Kaleida Graph (Synergy Software, Reading, Pa.). Rates were determined with a single exponential, and Michaelis Menten fits were completed as previously described in Kennedy et al. *Biochemistry* 48:11161-11168 (2009).

Test for Cytotoxicity of 3'-Deoxyadenosine (Adenosine Chain Terminator, rACT)

Human primary activated $CD4^+$ T cells, a human microglia cell line, CHME5 (Jamburuthugoda et al. *J. Biol. Chem.* 283:9206-9216 (2008)), and a human monocytic cell line, U937 (NIH AIDS Research and Reference Reagent Program), were cultured as previously described. For isolating $CD4^+$ T cells, human PBMC were harvested from Ficoll density gradients (Lymphoprep, Axis-Shield PoC AS, Oslo, Norway) from buffy coat purchased from NY Blood Center, and monocytes were then purified using immunomagnetic selection with anti-CD14 antibody conjugated magnetic beads, following the manufacturer's recommendations (Miltenyi Biotech, Auburn, Calif.). $CD4^+$ T lymphocytes were isolated from the monocyte-depleted buffy coats after immunomagnetic selection and cultured with IL-2 (NIH AIDS Research and Reference Reagent Program) for activation. CHME5, U937 and human primary activated $CD4^+$ T cells were cultured in the presence and absence of varying concentrations of rACT for 48 hr, and the percentages of live and dead cells were analyzed by both FACS analysis and trypan blue staining.

Transduction Assays for Inhibition of HIV-1 Infection and Proviral DNA Synthesis by rNCTs in Macrophages and T cells The purified human monocytes from three different donors were differentiated to macrophages as described previously, and D3HIV-GFP vector system expressing GFP, was also prepared as previously described in Jamburuthugoda et al. *J. Biol. Chem.* 281:13388-13395 (2006); Diamond et al. *J. Biol. Chem.* 279:51545-51553 (2004); Jamburuthugoda et al. *J. Biol. Chem.* 283:9206-9216 (2008); and Weiss et al. *Biochemistry* 43:4490-4500 (2004). Equal p24 level of the produced vector was used for infecting human macrophages pre-incubated with different concentrations of rACT (RI Chemicals, CA) for 12 hours. For ddUTP, the produced vector was pre-incubated for at least two hours. One half of the harvested cells were used for determining the percentages of the GFP expressing and/or propidium iodide (PI) stained cells by FACS at 7 days post infection. All cells used to asses transduction efficiency were gated or stained with propidium iodide to assure live cells were measured. The remaining cells were used for the extraction of genomic DNA. Quantitative 2LTR circle PCR assay using real-time PCR was normalized by total genomic DNA (Biorad, Hercules, Calif.). The primers and amplification protocol were previous described in Jamburuthugoda et al. *J. Biol. Chem.* 281:13388-13395 (2006); and Skasko and Kim, *J. Virol.* 82: 7716-7720 (2008).

rACT was tested in T cells as follows, human primary activated $CD4^+$ T cells ($2.5 \times 10^5$) cells isolated from two donors were pre-treated with 0, 0.1, and 1 mM rACT for 4 hours, and then the cells were transduced with DHIV-GFP. The transduced cells were fixed at 48 hours post transduction, and analyzed by FACS for determining the percent of GFP cells. The analysis was conducted in duplicate per donor, and the means and standard deviations were derived from all data obtained.

ddUTP was tested in T cells as follows, human primary activated $CD4^+$ T cells ($2.5 \times 10^5$) cells isolated from two donors were pre-treated with 0, 0.01, 0.1 and 1 mM ddUTP for at least 2 hours, and then the cells were transduced with DHIV-GFP. The transduced cells were prepared 48 hours post transduction, and analyzed by FACS for determining the percent of GFP cells. The analysis was conducted in triplicate per donor, and the means and standard deviations were derived from all data obtained.

Inhibition of HIV-1 Infection and by rNCTs in Macrophages

Human primary macrophages derived from monocytes ($5 \times 10^5$ cells) were infected with M-tropic HIV-1 YU-2 (MOI of 0.05) and cultured for 12 days. Half of the supernatant was collected every 3 days and replaced with a fresh media containing 0, 0.1, 1, and 2 mM rNCT. The HIV-1 p24 levels in the collected supernatant samples were determined by p24 ELISA.

Other Embodiments

From the foregoing description, it will be apparent that variations and modifications may be made to the invention described herein to adopt it to various usages and conditions. Such embodiments are also within the scope of the following claims.

The recitation of a listing of elements in any definition of a variable herein includes definitions of that variable as any single element or combination (or subcombination) of listed elements. The recitation of an embodiment herein includes that embodiment as any single embodiment or in combination with any other embodiments or portions thereof.

INCORPORATION BY REFERENCE

All patents and publications mentioned in this specification are herein incorporated by reference to the same extent as if each independent patent and publication was specifically and individually indicated to be incorporated by reference.

What is claimed is:

1. A method for inhibiting retrovirus replication in a subject, the method comprising administering to a non-dividing cell of a subject having or at risk of developing a retroviral infection a ribonucleoside chain terminator or an analog or derivative thereof, thereby inhibiting viral replication in the non-dividing cell of the subject.

2. The method of claim 1 further comprising administering to the subject at least one additional anti-retroviral agent, thereby inhibiting viral replication in the subject.

3. The method of claim 1, wherein the subject is human.

4. The method of claim 2, wherein the anti-retroviral agent is selected from the group consisting of a nucleoside reverse transcriptase inhibitor, a nucleotide reverse transcriptase inhibitor, a non-nucleoside reverse transcriptase inhibitor, a protease inhibitor, a fusion inhibitor, and an integrase inhibitor.

5. The method of claim 4, wherein the nucleoside reverse transcriptase inhibitor is selected from the group consisting of zidovudine, didanosine, stavudine, lamivudine, abacavir, apricitabine, emtricitabine, entecavir, zalcitabine, dexelvucitabine, alovudine, amdoxovir, elvucitabine, AVX754, BCH-189, phosphazid, racivir, SP1093V, stampidine, phosphonovir, idoxuridine, and analogs or derivatives thereof.

6. The method of claim 4, wherein the nucleotide reverse transcriptase inhibitor is selected from the group consisting of tenofovir, adefovir, and analogs or derivatives thereof.

7. The method of claim 4, wherein the non-nucleoside reverse transcriptase inhibitor is selected from the group consisting of foscarnet, efavirenz, nevirapine, delavirdine, etravirine, and analogs or derivatives thereof.

8. The method of claim 4, wherein the protease inhibitor is selected from the group consisting of invirase, fortovase, norvir, crixivan, viracept, agenerase, kaletra, reyataz, fosamprenavir, tipranavir, saquinavir, ritonavir, indinavir, nelfinavir, amprenavir, lopinavir, atazanavir, darunavir, and analogs or derivatives thereof.

9. The method of claim 4, wherein the fusion inhibitor is selected from the group consisting of maraviroc, enfuvirtide, and analogs or derivatives thereof.

10. The method of claim 4, wherein the integrase inhibitor is selected from the group consisting of raltegravir, elvitegravir, and analogs or derivatives thereof.

11. The method of claim 1, wherein the retrovirus is human immunodeficiency virus.

* * * * *